US006200752B1

(12) United States Patent
Lakowicz

(10) Patent No.: US 6,200,752 B1
(45) Date of Patent: Mar. 13, 2001

(54) METHOD AND COMPOSITION FOR DETECTING THE PRESENCE OF A NUCLEIC ACID SEQUENCE IN A SAMPLE

(76) Inventor: Joseph R. Lakowicz, 10037 Fox Den Rd., Ellicott City, MD (US) 21042

( * ) Notice: Subject to any disclaimer, the term of this patent is extended or adjusted under 35 U.S.C. 154(b) by 0 days.

(21) Appl. No.: 09/007,064

(22) Filed: Jan. 14, 1998

(51) Int. Cl.[7] ............................. C12Q 1/68; C07H 21/02; C07H 21/04; C12N 15/00
(52) U.S. Cl. ........................... 435/6; 536/23.1; 536/24.3; 935/76; 935/77; 935/78
(58) Field of Search ............................. 435/3; 536/23.1, 536/24.3; 935/76, 77, 78

(56) References Cited

U.S. PATENT DOCUMENTS

| | | | |
|---|---|---|---|
| 5,196,510 | * 3/1993 | Rodwell et al. | 530/324 |
| 5,262,526 | * 11/1993 | Sasamoto et al. | 534/551 |
| 5,559,214 | * 9/1996 | Delecki et al. | 534/10 |
| 5,591,578 | * 1/1997 | Meade et al. | 435/6 |
| 5,660,991 | * 8/1997 | Lakowicz et al. | 435/7.1 |
| 5,663,319 | * 9/1997 | Bittner et al. | 536/24.3 |
| 5,760,191 | * 6/1998 | Snow et al. | 534/10 |
| 5,827,663 | * 10/1998 | Affleck et al. | 435/6 |
| 5,840,482 | * 11/1998 | Gray et al. | 435/6 |
| 5,869,255 | * 2/1999 | Mathies et al. | 435/6 |

OTHER PUBLICATIONS

Denijn et al., In Situ Hybridization : A Valuable Tool in Diagnostic Pathology. AMPIS 100 : 669–681 (1992).*
Collins et al., J. of Forensic Sciences 39(6) : 1347–1355 (1994).*
Guo et al., "A Long–Lived, Highly Luminescent Re (I) Metal Ligand complex as a Biomolecular Probe", Analytical Biochemistry 254 : 179–186 (1997).*
Collins et al., "Identification of Sperm and Non–sperm Male Cells in Cervicovaginal Smears Using Fluorescence in situ Hybridization: Applications in Alleged Sexual Assault Cases", J. of Forensic Sciences 39(6) : 1347–1355 (1994).*
Malak et al., "Long–Lifetime Metal–Ligand Complexes as Luminescent probes for DNA", J. of Fluorescence 7(2): 107–112 (1997).*
Demas et al., "Applications of Luminescent Transition Metal Complexes to Senor Technology and Molecular Probes", J. of Chem. Educ. 74(6) : 690–695 (1997).*
Dirks et al., "Simultaneous Detection of Different mRNA Sequences Coding for Neuropeptide Hormones by Double in Situ Hybridization Using FITC– and Biotin–labeled Oligonucleotides", The Journal of Histochemistry and Cytochemistry 38(4) : 467–473 (1990).*
Zhang et al., "Genetic Typing by Capillary Electrophoresis with the Allelic Ladder as an Absolute Standard", Analytical Chemistry 68 :2927–2931 (1996).*
Voskova–Goldman et al., "DMD–specific FISH Probes are Diagnostically Useful in the Detection of Female Carriers of DMD Gene Deletions", Neurology 48 :1633–1638 (1997).*

Science/Technology, "DNA Chips Come Of Age After period of gestation, technology for genetic analysis is blossoming", pp. 42–44, Dec. 9, 1996 C&EN.
Molecular Probes, Inc., "The Leader In Innovative Fluorescence Technology, Reagents for Fluorescence In Situ Hybridization", brochure 7 pages.
Molecular Dynamics, "Fluroescence Imaging Application Guide", pp. 9 and 10.
Akira Murakami et al., Nucleic Acids Research, 1991 Oxford University Press, "Fluroescent–labeled oligonucleotide probes: detection of hybrid formation in solution by fluorescence polarization spectroscopy", vol. 19, No. 15, pp. 4097–4102.
G. Terrance Walker et al., Clinical Chemistry 42:1, 1996, "Strand displacement amplification (SDA) and transient–state fluorescence polarization detection Mycobacterium tuberculosis DNA", pp. 9–13.
E. Schröck et al., Science, vol. 273, "Multicolor Spectral Karyotyping of Human Chromosomes", Jul. 26, 1996, pp 494–498.
Ricki Lewis, Photonics Spectra, "Biophotonics In Action, Chromosone Charting Takes a Giant Step", pp 47–50, Jun. 1996.
J. Lawrence Fox et al., Clinical Chemistry, vol. 41, No. 11, Fluorescence in Situ Hybridization: Powerful Molecular Tool for Cancer Prognosis, pp. 1554–1559, (1995).
P.M. Nederlof et al., Cytometry 11, "Multiple Fluorescence In Situ Hybridization", pp. 126–131, (1990).
Majid Siadat–Pajouh et al., The Journal of Histochemistry and Cytochemistry, Introduction of a Fast and Sensitive Fluorescent In Situ Hybridization Method for Single–copy Detection of Human Papillomavirus (HPV) Genome, vol. 42, No. 11, pp. 1503–1512, 1994.

(List continued on next page.)

Primary Examiner—Ethan Whisenant
(74) Attorney, Agent, or Firm—Rothwell, Figg, Ernst & Manbeck

(57) ABSTRACT

A method for detecting the presence of a nucleic acid sequence in a sample includes the step of coupling a fluorescent metal-ligand complex to an oligonucleotide having a sequence complementary to the nucleic acid sequence to form a probe. The probe is added to a sample that contains the nucleic acid sequence to form a mixture containing a reaction product. The mixture is exposed to an exciting amount of radiation. The fluorescence of the metal-ligand complex is detected, and the presence of the nucleic acid sequence is determined based on the fluorescence of the metal-ligand complex. A composition for detecting the presence of a nucleic acid sequence, includes a fluorescent metal-ligand complex coupled to an oligonucleotide having a sequence complementary to the nucleic acid sequence. A diagnostic kit for detecting the presence of a nucleic acid sequence, includes a fluorescent metal-ligand complex coupled to an oligonucleotide having a sequence complementary to the nucleic acid sequence.

3 Claims, 22 Drawing Sheets

OTHER PUBLICATIONS

William G. Kearns et al., Methods in Molecular Biology, vol. 33, Chapter 2, "Fluorescent In Situ Hybridization Using Chromosome–Specific DNA Libraries", pp. 15–23, 1994.

D.C. Tkachuk et al., GATA 8(2), "Clinical Applications of Fluorescence in situ Hybridization", pp. 67–74, (1991).

Marylene Denijn et al, APMIS 100, "In situ hybridization: A valuable tool in diagnostic pathology", pp. 669–681, 1992.

John A. McNeil et al., GATA 8(2), "In Situ Hybridization", pp. 41–58, 1991.

Trude Schwarzacher et al., Methods in Molecular Biology, vol. 28, Chapter 26, Direct Fluorochrome–Labeled DNA Probes for Direct Fluorescent In Situ Hybridization to Chromosomes, pp. 167–176.

Ian Durrant et al., Histochemical Journal 27, "Fluorescein as a label for non–radioactive in situ hybridization", pp. 94–99, 1995.

Jayne A. Mathews et al., Analytical Biochemistry 169, "Analytical Strategies of the Use of DNA Probes", pp. 1–25, 1988.

Ursula E.M. Gibson et al., Genome Research, "Genome Methods A Novel Method for Real Time Quantitative RT–PCR", pp. 995–1001, 1996.

Roy A. Swiger et al., Environmental and Molecular Mutagenesis 27, "Fluorescence In Situ Hybridization", pp. 245–254, 1996.

Jacqueline A. Fidanza et al., J. Am. Chem. Soc. 111, "Introduction of Reporter Groups at Specific Sites in DNA Containing Phosphorothioate Diester", pp. 9117–9119, 1989.

Kyoji Ueno et al., Analytical Cheimistry, vol. 66, No. 9, "Simultaneous Monitoring of DNA Fragments Separated by Electrophoresis in a Multiplexed Array of 100 Capillaries", pp. 1424, May 1, 1994.

Henryk Szmacinski et al., Methods in Enzymology, vol. 240, "Fluorescence Lifetime Imaging Microscopy: Homodyne Technique Using High–Speed Gated Image Intensifier", 723–748, 1994.

J.R. Lakowicz, et al., Cell Calcium, vol. 15, "Fluorescence lifetime imaging of intracellular calcium in COS cells using Quin–2", pp. 7–27, 1994.

J.R. Lakowicz, et al., Journal of Fluorescence, vol. 4, No. 1, "Emerging Biomedical and Advanced Application of Time–Resolved Fluorescence Spectroscopy", pp. 117–136, 1994.

J. R. Lakowicz, et al., Analytical Biochemistry, 202, "Fluorescence Lifetime Imaging", pp. 316–330, 1992.

J.R. Lakowicz, et al., Proc. Natl., Acad., Sci., vol. 89, "Fluorescence lifetime imaging of free and protein–bound NADH", pp. 1271–1275, Feb. 1992.

Stephen P.A. Fodor, Science, vol. 277, "DNA Sequencing Massively Parallel Genomics", pp. 393, Jul. 18, 1997.

Ann Caviani Pease et al., Proc. Natl. Acad. Sci., vol. 91, "Light–generated oligonucleotide arrays for rapid DNA sequence analysis", pp. 5022, May 1994.

R.J. Lipshutz et al., BioFeature, vol. 19, No. 3, "Using Oligonucleotide Probe Arrays To Access Genetic Diversity", pp. 442, 1995.

Maureen T. Cronin et al., Human Mutation, 7, "Cystic Fibrosis Mutation Detection by Hybridization to Light–Generated DNA Probe Arrays", pp. 244, 1996.

Xiaohua C. Huang et al., Anal. Chem., vol. 64, "DNA Sequencing Using Capillary Array Electrophoresis", pp. 2149, 1992.

Swerdlow et al., Anal. Chem., vol. 63, "Three DNA Sequencing Methods Using Capillary Gel Electrophoresis and Laser–Induced Fluorescence", pp. 2835, 1991.

S. Carson et al., Anal. Chem., vol. 65, "DNA Sequencing by Capillary Electrophoresis: Use of a Two–Laser–Two–Window Intensified Diode Array Detection System", pp. 3219, 1993.

L.R. Middendorf et al., American Biotechnology Laboratory, "Large scale DNA sequencing", pp. 2.

John A. Brumbaugh et al., Proc. Natl. Acad. Sci., vol. 85, "Continuous, on–line DNA sequencing using oligodeoxynucleotide primers with multiple fluorophores", pp. 5610, Aug. 1988.

The Stratgene Catalog. Gene Characterization Kits. 1988, p. 39.

* cited by examiner

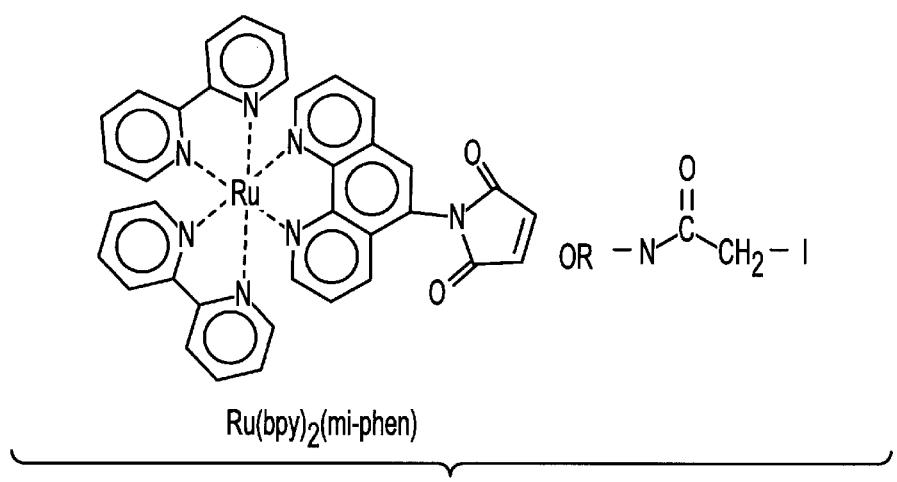
Ru(bpy)₂(mi-phen)
FIG. 9A
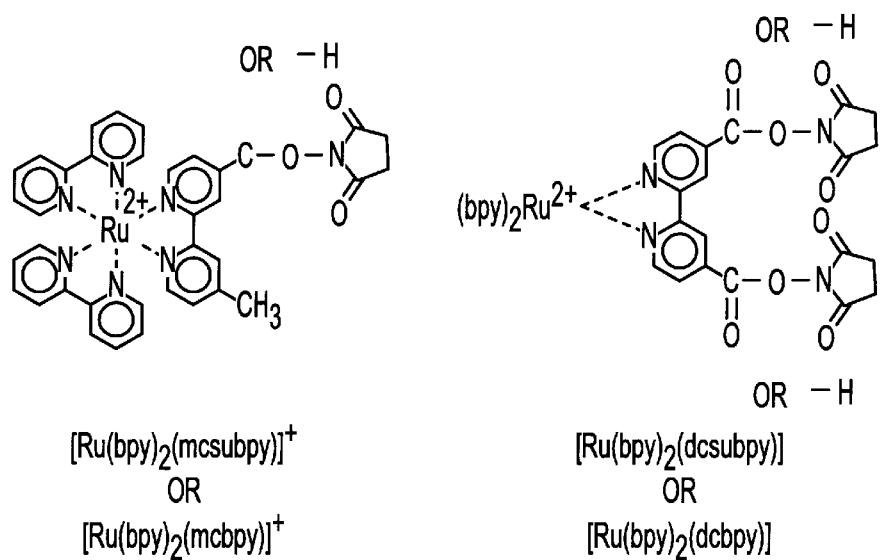
[Ru(bpy)₂(mcsubpy)]⁺
OR
[Ru(bpy)₂(mcbpy)]⁺
FIG. 9B
[Ru(bpy)₂(dcsubpy)]
OR
[Ru(bpy)₂(dcbpy)]
FIG. 9C
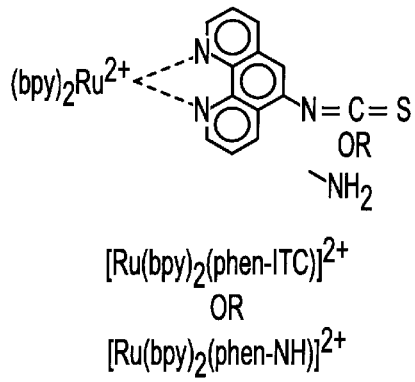
[Ru(bpy)₂(phen-ITC)]²⁺
OR
[Ru(bpy)₂(phen-NH)]²⁺
FIG. 9D

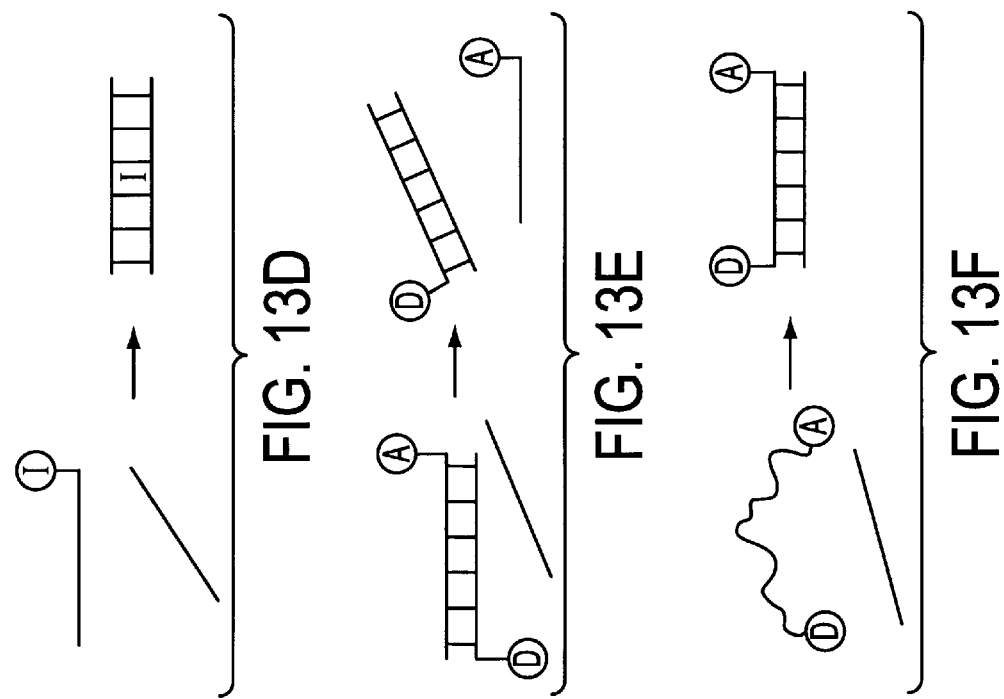
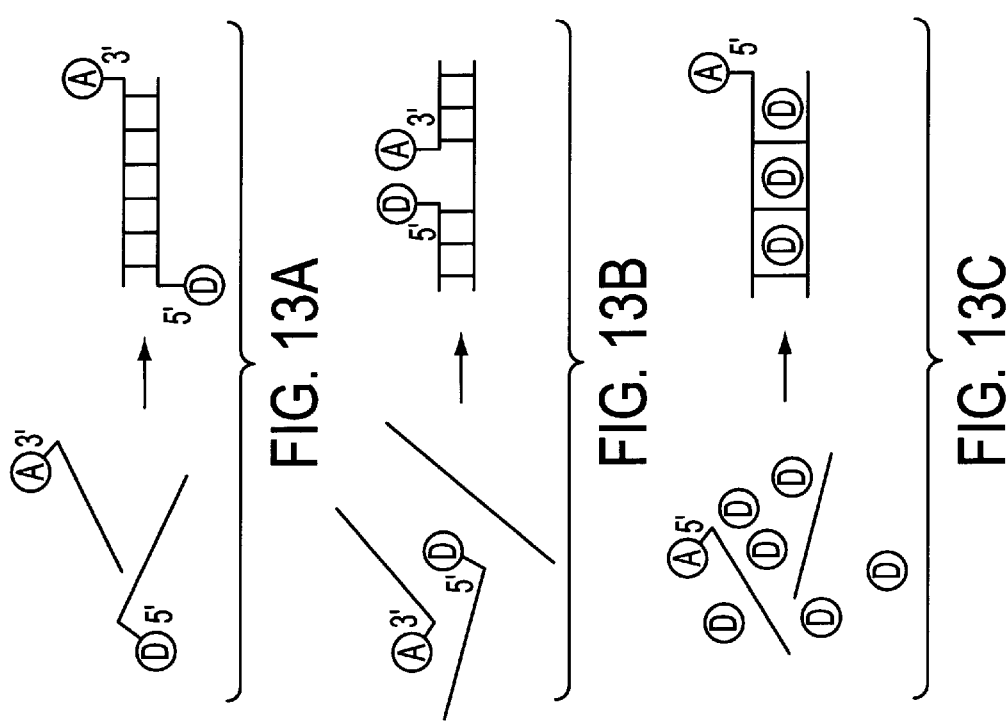

Ru(bpy)₂(dppz) (PF₆)2

Os(dppz)(dppb)₂

Os(dppz)(dppe)₂

METHOD AND COMPOSITION FOR DETECTING THE PRESENCE OF A NUCLEIC ACID SEQUENCE IN A SAMPLE

BACKGROUND OF THE INVENTION

1. Field of the Invention

The present invention is in the field of detecting the presence of a nucleic acid sequence in a sample.

2. Description of the Background Art

Fluorescence in situ hybridization ("FISH") is widely used in medical diagnostics. Present technology for in situ hybridization includes the use of fluorescence probes such as fluorescein and rhodamine and detection of hybridized DNA by localization of the product of an enzyme catalyzed reaction.

The following references describe known fluorescence in situ hybridization techniques:

Swiger, R. R., and Tucker, J. D., "Fluorescence In Situ Hybridization: A Brief Review," *Environmental and Molecular Mutagenesis* 27:245–54 (1996).

Schrock, E., du Manoir, S., Veldman, T., Schoell, B., Wienberg, J., Ferguson-Smith, M. A., Ning, Y., Dedbetter, D. H., Bar-Am, I., Soenksen, D., Garini, Y., and Ried, T., "Multicolor Spectral Karyotyping of Human Chromosomes," *Science* 273:494–98 (1996).

Lewis, R., "Chromosome Charting Takes a Giant Step," *Photonics Spectra* 48–50 (1996).

Fox, J. L., Hsu, P., Legator, M., Morrison, L. E., and Seelig, S. A., "Fluorescence In Situ Hybridization: Powerful Molecular Tool for Cancer Prognosis," *Clinical Chemistry* 41:1554–59 (1995).

Nederlof, P. M., van der Flier, S., Wiegant, J., Raap, A. K., Tanke, H. J., Ploem, J. S., and van der Ploeg, M., "Multiple Fluorescence In Situ Hybridization," *Cytometry* 11:126–31 (1990).

Siadat-Pajouh, M., Ayscue, A. H., Periasamy, A., and Herman, B., Introduction of a Fast and Sensitive Fluorescent In Situ Hybridization Method for Single-copy Detection of Human Papillomavirus (HPV) Genome," *The Journal of Histochemistry and Cytochemistry* 42:1503–12 (1994).

Kearns, W. G. and Pearson, P. L., "Fluorescent In Situ Hybridization Using Chromosome-Specific DNA Libraries," *Methods in Molecular Biology* 33:15–22 (1994).

Tkachuk, D. C., Pinkel, D., Kuo, W., Weier, H., and Gray, J. W., "Clinical Applications of Fluorescence in situ Hybridization," *GATA* 8(2):67–74 (1991).

Denijn, M., Schuurman, H., Jacobse, K. C., and Weger, R. A., "In Situ hybridization: A valuable tool in diagnostic pathology," *APMIS* 100:669–681 (1992).

McNeil, J. A., Villnave Johnson, C., Carter, K. C., Singer, R. H., and Bentley Lawrence, J., "In Situ Hybridization," *GATA* 8(2):41–58 (1991).

Schwarzachter, T., and Heslop-Harrison, J. S., "Direct Fluorochrome-Labeled DNA Probes for Direct Fluorescent In Situ Hybridization of Chromosomes," *Methods in Molecular Biology, Vol. 28: Protocols for Nucleic Acid Analysis by Nonradioactive Proves* 167–76 (1994).

Durrant, J., Brunning, S., Eccleston, L., Chadwick, P., and Cunningham, M., "Fluorescein as a label for non-radioactive in situ hybridization," *Histochemical Journal* 27:94–99 (1995).

None of these papers mentions the use of metal-ligand complexes in fluorescence in situ hybridization to detect the presence of a nucleic acid.

One limitation of prior art DNA hybridization is the low levels of light available from commonly used fluorophores, the presence of significant background fluorescence which limits sensitivity, and photobleaching of the probes. The resulting fluorescence is typically on a nanosecond time scale, which is also the decay time of the commonly used fluorophores. In addition, the commonly used fluorophores display small Stoke's shifts making it difficult to detect their fluorescence in the presence of a fluorescent background. There is also a need for fluorophores with greater resistance to fading and increased shelf life, i.e., archivability of the slides.

There is extensive literature regarding the spectral properties of metal-ligand complexes. The following is a list of papers regarding metal-ligand complexes:

Maestri, M., Sandrini, D., Balzani, V., Maeder, U. and von Zelewsky, "Absorption Spectra, Electrochemical Behavior, Luminescence Spectra, and Excited-State Lifetimes of Mixed-ligand Ortho-Metalated Rhodium (III) Complexes," *Inorg. Chem.*, 26:1323–1327 (1987).

Sutin, N. and Creutz, C., "Properties and Reactivities of the Luminescent Excited States of Polypyridine Complexes of Ruthenium(II) and Osmium(II)," *Inorg. & Organometall. Photochem.*, Chap. 1, pp. 1–27 (1978).

Hager, G. D., Watts, R. J. and Crosby, G. A., "Charge-transfer Excited States of Ruthenium(II) Complexes. Relationship of Level Parameters to Molecular Structure," *J. Am. Chem. Soc.*, 97;7037–7042 (1975).

Orellana, G. and Braun, A. M., "Quantum Yields of $^3$MLCT Excited State Formation and Triplet-Triplet Absorption Spectra of Ruthenium(II) Tris-Chelate Complexes Containing Five- and Six-Membered Heterocyclic Moieties," *J. Photochem. Photobiol. A. Chem..*, 48:277–289 (1989).

Harrigan, R. W. and Crosby, G. A., "Symmetry Assignments of the Lowest CT Excited States of Ruthenium (II) Complexes Via a Proposed Electronic Coupling Model," *J. Chem. Phys.*, 59(7):3468–3476 (1973).

Yersin, H. and Braun, D., "Isotope-Induced Shifts of Electronic Transitions: Application to $[Ru(bpy-h_8)_3]^{2+}$ and $[Ru(bpy-d_8)_3]^{2+}$ in $[Zn(bpy-h_8)^3](ClO_4)_2$," *Chem. Phys. Letts.*, 179(1,2):85–94 (1991).

Coe, B. J., Thompson, D. W., Culbertson, C. T., Schoonover, J. R. and Meyer, T. J., "Synthesis and Photophysical Properties of Mono(2,2',2'-Terpyridine) Complexes of Ruthenium(II)," *Inorg. Chem.*, 34:3385–3395 (1995).

Lees, A. J., "Luminescence Properties of Organometallic Complexes," *Chem. Rev.*, 87:711–743 (1987).

DeArmond, M. K. and Carlin, C. M., "Multiple State Emission and Related Phenomena in Transition Metal Complexes," *Coordination Chem. Rev.*, 36:325–355 (1981).

Kondo, T., Yanagisawa, M. and Fujihira, M., "Single Exponential Decay for the Luminescence Intensity of $Ru(bpy)_3^{2+}$ Complex in Langmuir-Blodgett Films," *Chem. Letts.*, 1639–1993 (1993).

None of the above references suggest use of metal-ligand complexes in fluorescence in situ hybridization.

There remains a need in the art for improved methods of detecting the presence of nucleic acid sequences.

SUMMARY OF THE INVENTION

In accordance with the present invention, a method for detecting the presence of a nucleic acid sequence in a sample includes the step of coupling a fluorescent metal-ligand complex to an oligonucleotide having a sequence, complementary to the nucleic acid sequence to form a probe. The probe is added to a sample that contains the nucleic acid sequence to form a mixture containing a reaction product. The mixture is exposed to an exciting amount of radiation. The fluorescence of the metal-ligand complex is detected, and the presence of the nucleic acid sequence is determined based on the fluorescence of the metal-ligand complex.

Also in accordance with the present invention a composition for detecting the presence of a nucleic acid sequence includes a fluorescent metal-ligand complex coupled to an oligonucleotide having a sequence complementary to the nucleic acid sequence.

Further in accordance with the present invention a diagnostic kit for detecting the presence of a nucleic acid sequence includes a fluorescent metal-ligand complex coupled to an oligonucleotide having a sequence complementary to the nucleic acid sequence.

BRIEF DESCRIPTION OF THE DRAWINGS

FIG. 9 shows metal-ligand complexes which are reactive with sulfhydryl or amino groups and hence can be coupled to nucleic acids.

FIG. 13 graphically depicts methods to detect DNA hybridization by energy transfer. "D" is the donor, "A" is the acceptor or quencher, and "I" is the intercalating dye. The dyes can be free dyes, which intercalate as in FIG. 13(c), or covalently bound intercalators as in FIG. 13(d).

DETAILED DESCRIPTION OF THE INVENTION

Figure 1:
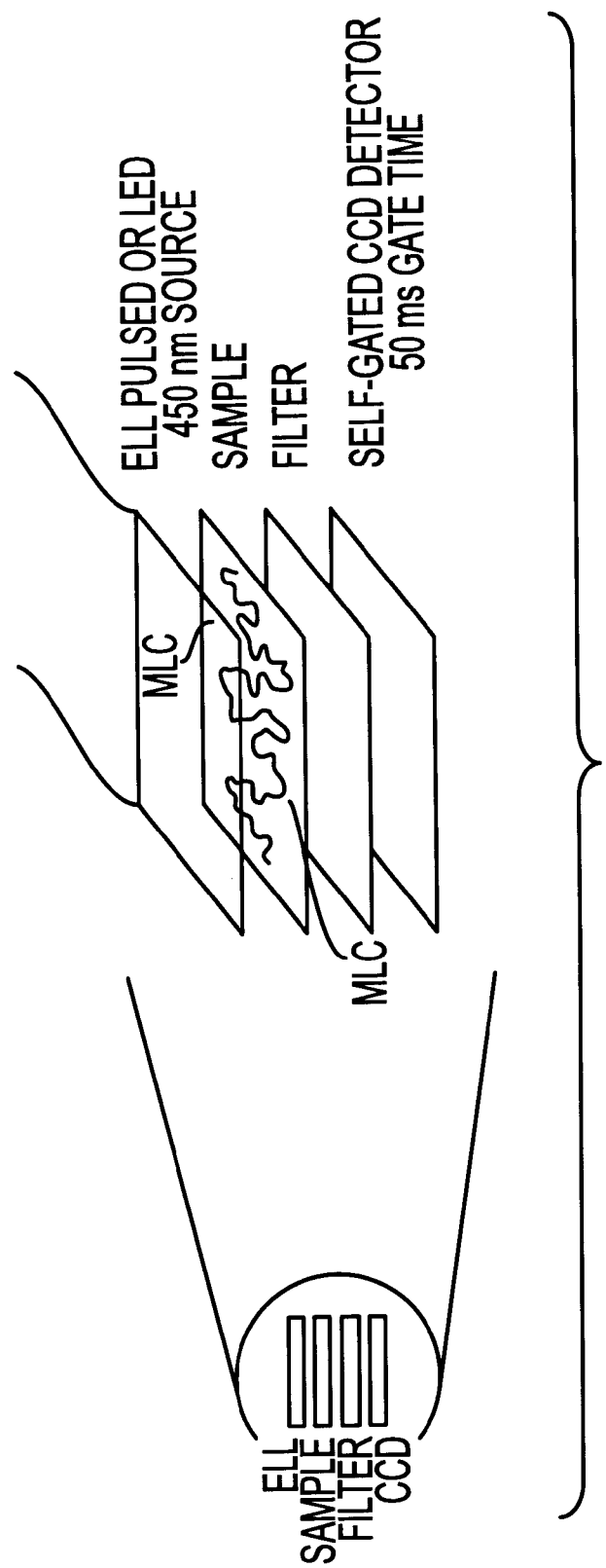
FIG. 1 schematically shows an instrument based on a simple light source and a CCD detector. This figure shows aspects of the invention based on the spectral properties of the metal-ligand complexes. The simple light source is pulsed at sufficient speed, and the detector is gated to provide high sensitivity imaging with suppression of background fluorescence.
Figure 2:
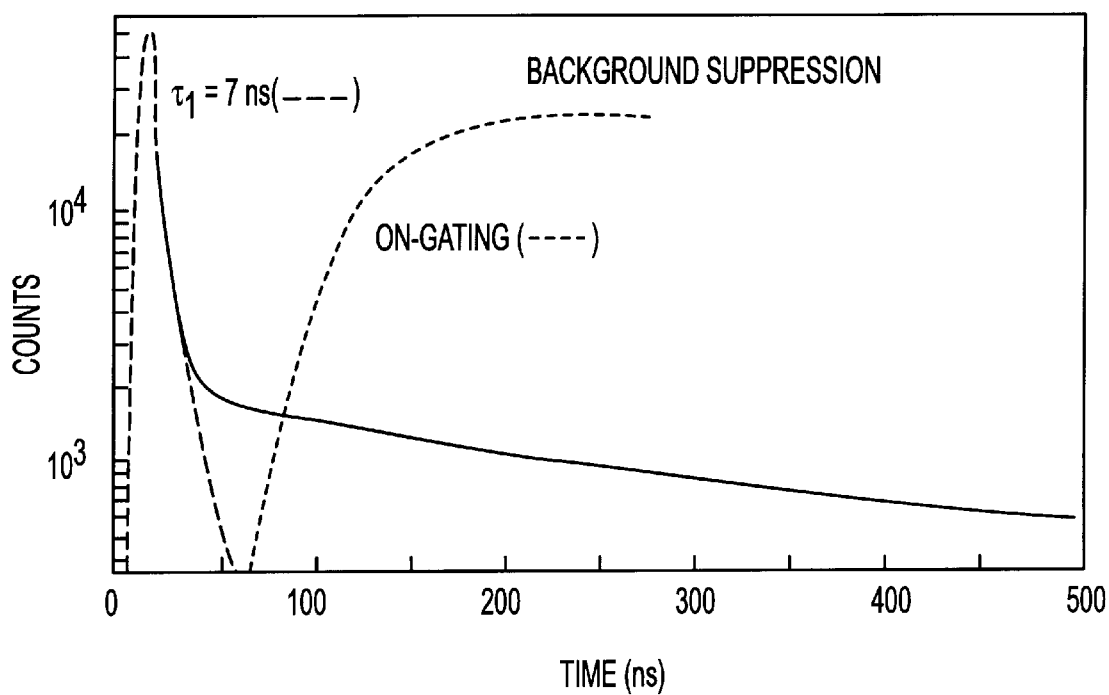
FIG. 2 is a graph depicting background suppression with a long lifetime metal-ligand complex.
Figure 3:
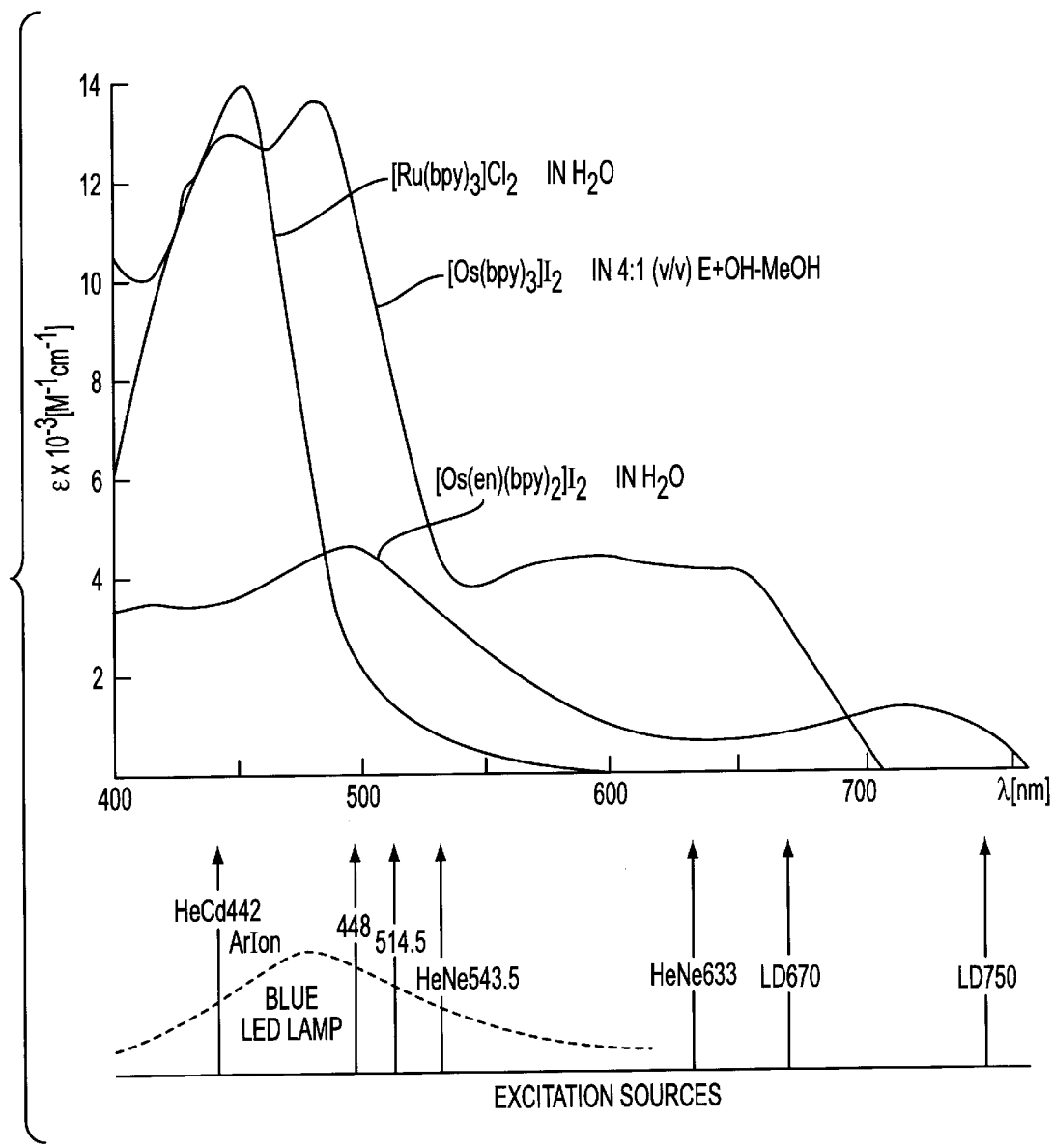
FIG. 3 graphically shows exciting metal-ligand complexes with a wide variety of simple light sources.
Figure 4:
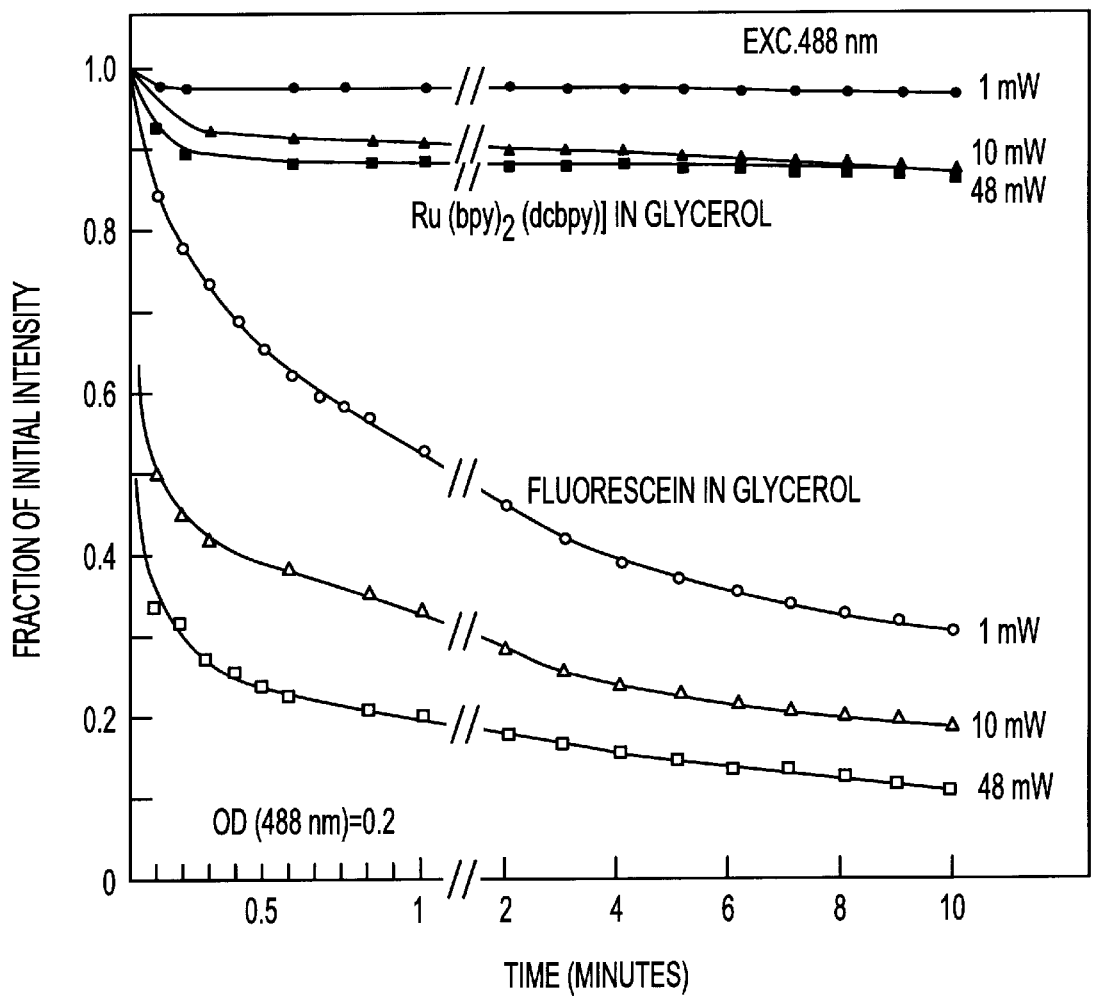
FIG. 4 graphically shows the high photochemical stability of the metal-ligand complexes. The high photochemical stability increases detection sensitivity and allows detection of the smallest number of gene copies in a chromosome sample. The high chemical stability of the metal-ligand complexes facilitates archiving pathology samples for future analysis.
Figure 5A:
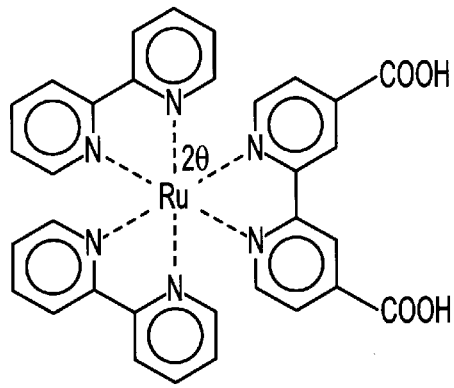
FIG. 5 graphically shows that the emission maximum of the metal-ligand complex can be altered by selection of the metal. Spectral karyotyping or multiplex FISH allow the identification of all 23 human chromosomes based on the emission spectra of the FISH probes. Metal-ligand complexes may be used in spectral karyotyping or multiplex FISH by utilizing metals with distinct emission spectra.
Figure 5B:
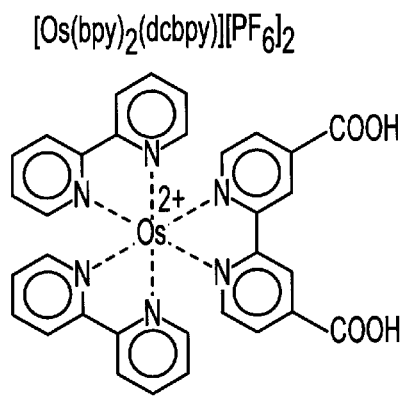
Figure 5C:
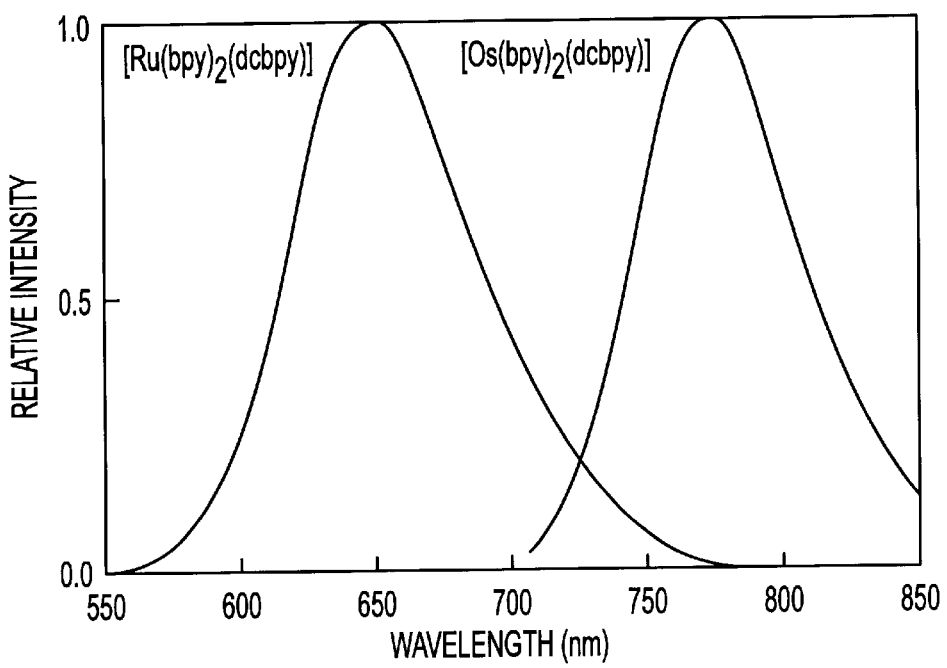
Figure 6:
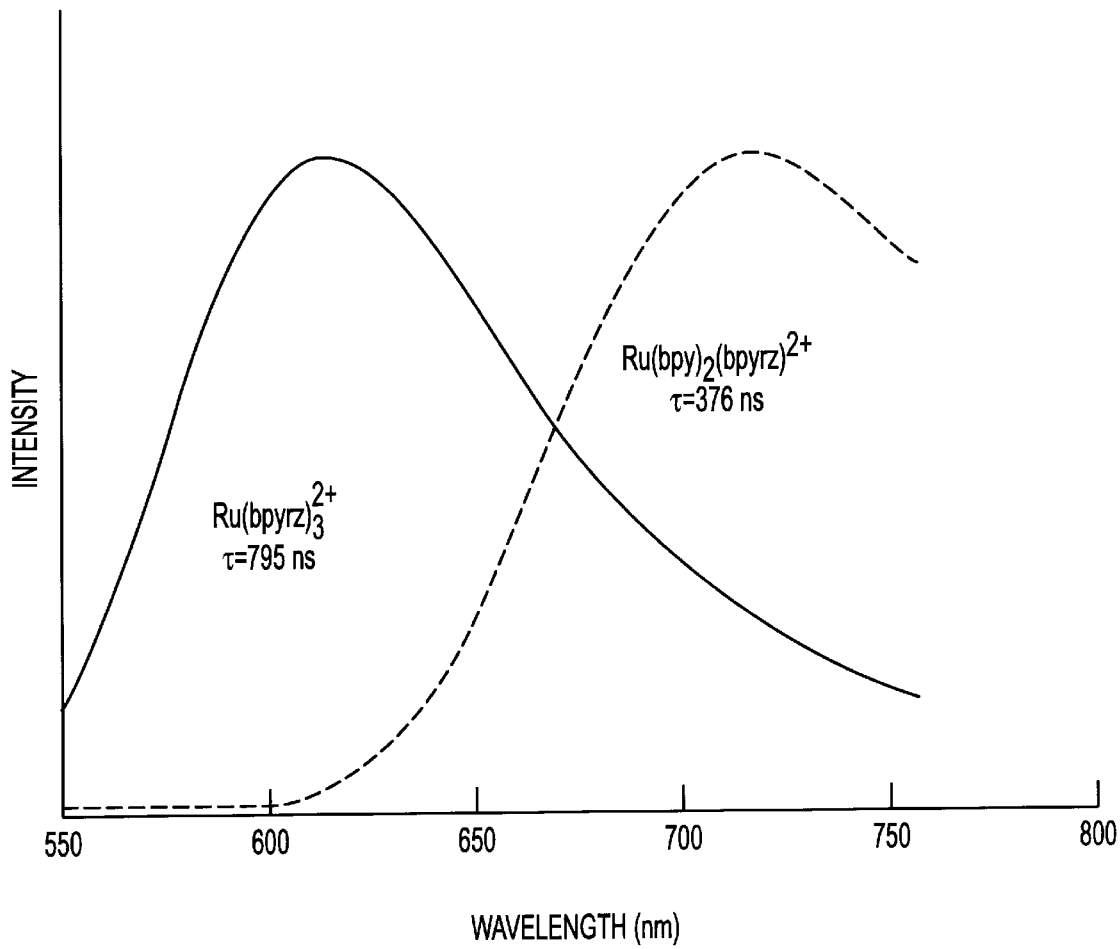
FIG. 6 graphically shows that the decay time of a metal-ligand complex can be altered by selection of the ligand. Lifetime imaging using metal-ligand complexes may be used to distinguish sites on a chromosome.
Figure 7:
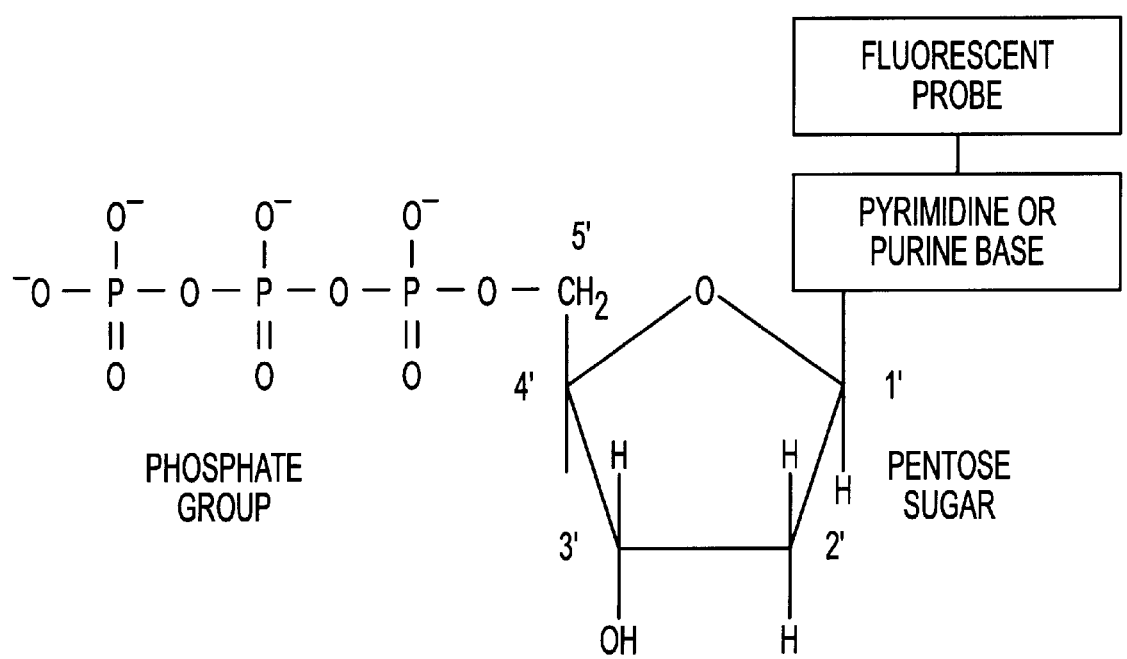
FIG. 7 is a formula representation of a fluorescent nucleotide for use in FISH. A fluorophore can be attached to the base.
Figure 8A:
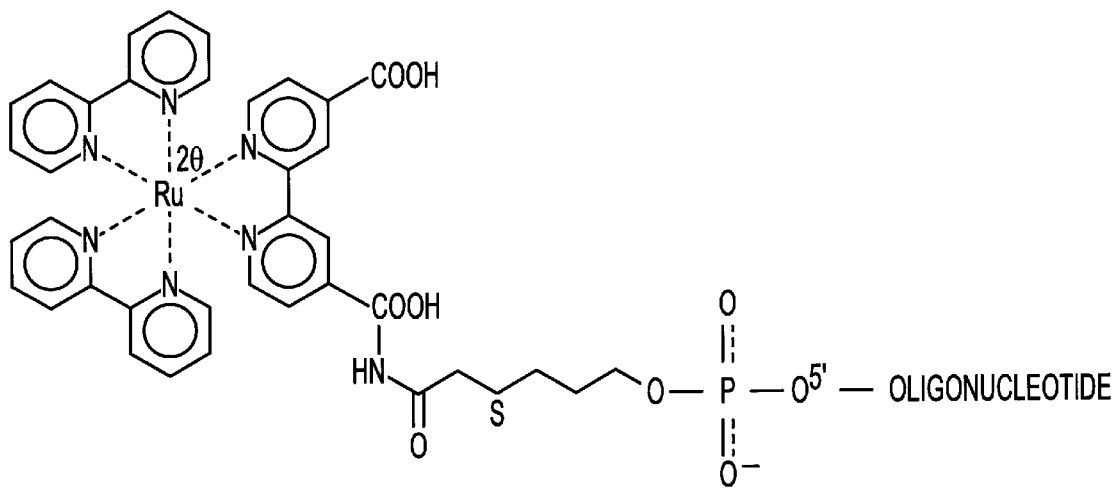
FIG. 8 depicts compounds for labeling DNA. DNA can be labeled using fluorescent primers (top) or using labeled nucleotide triphosphates. DNA can also be labeled on the 5' end via a thiophosphate linkage.
Figure 8B:
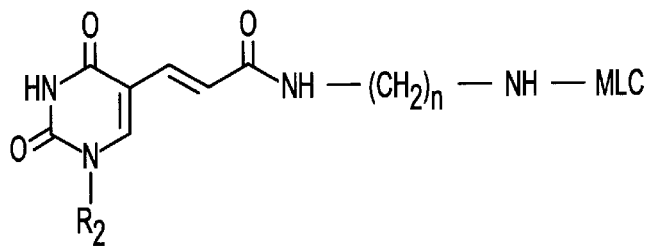
Figure 8C:
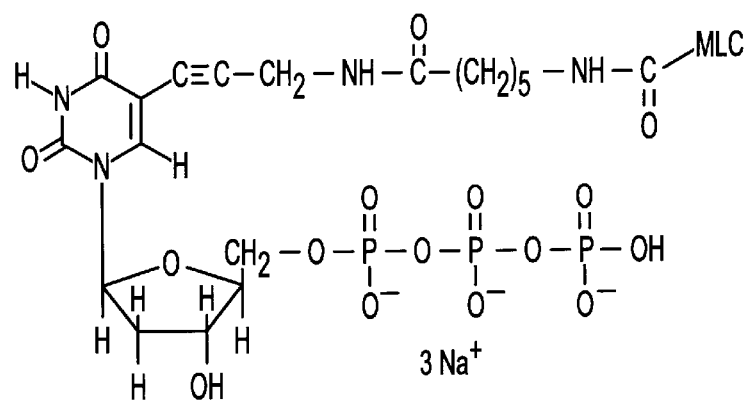
Figure 10:
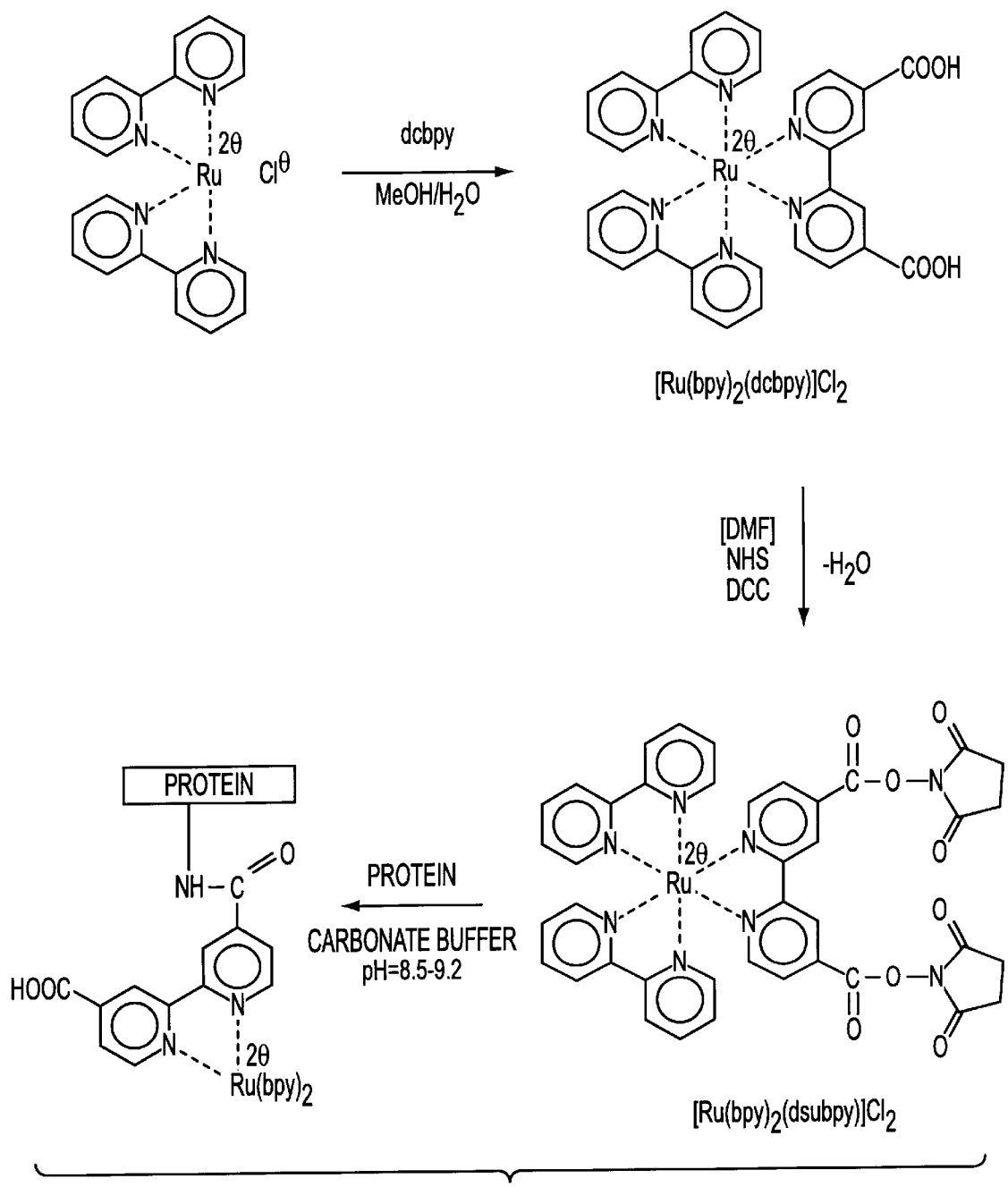
FIG. 10 depicts a representative synthesis of one reactive metal-ligand complex.
Figure 11A:
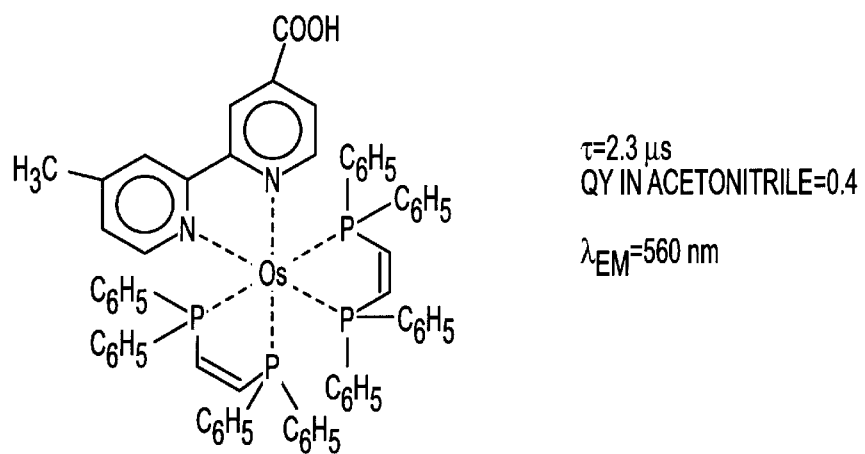
FIGS. 11 and 12 describe show spectral properties of other metal-ligand complexes. These figures show that one can obtain high quantum yield metal-ligand complexes for high sensitivity detection.
Figure 11B:
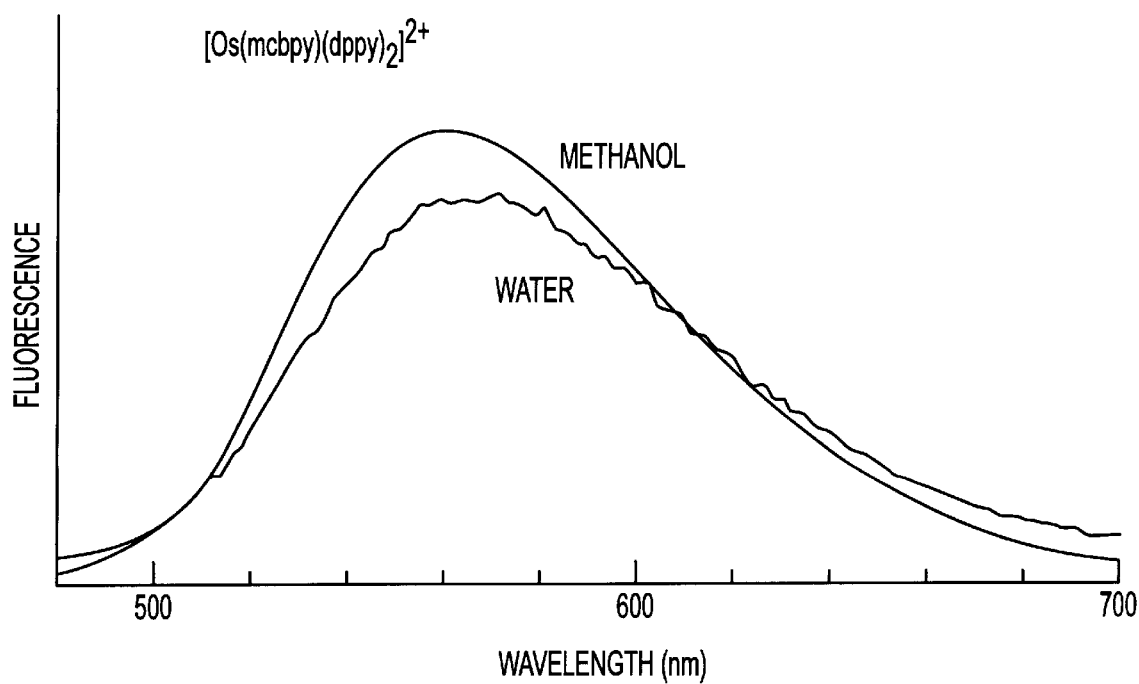
Figure 12A:
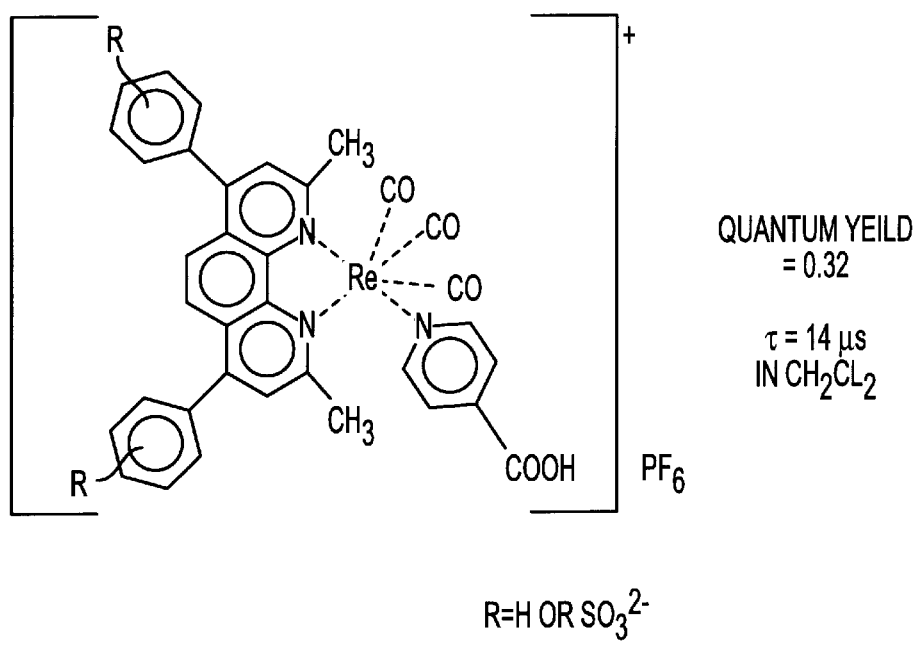
Figure 12B:
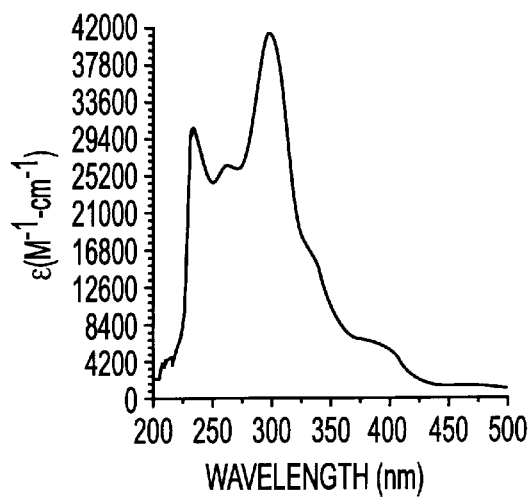
Figure 12C:
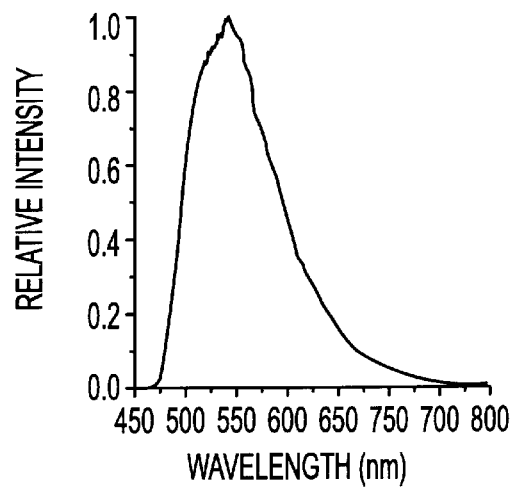
Figure 14A:
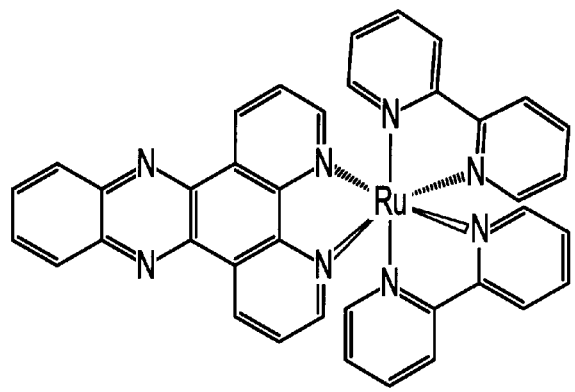
FIG. 14 depicts metal-ligand complexes containing the dppz ligand which can intercalate into double helical DNA.
Figure 14B:
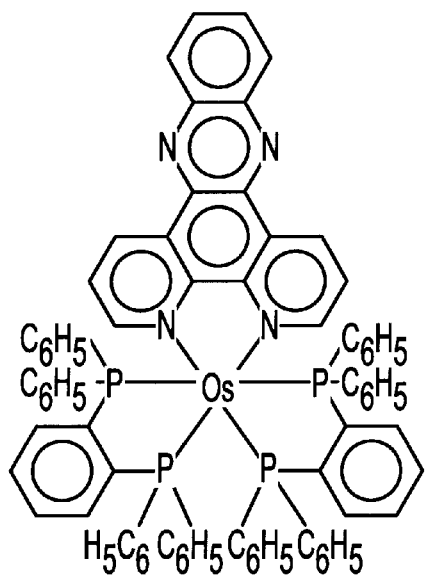
Figure 14C:
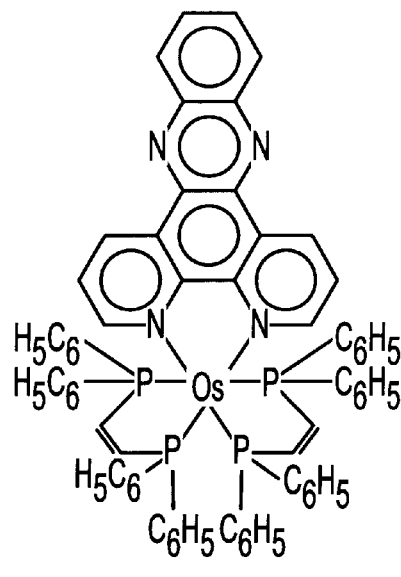
Figure 15A:
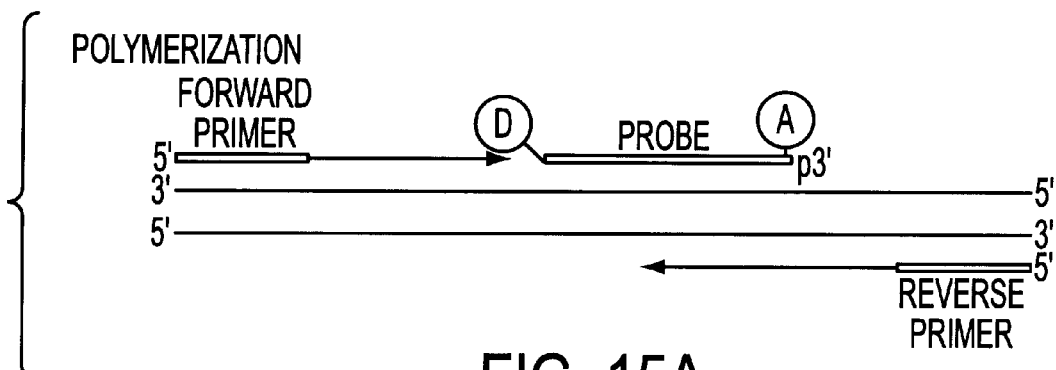
FIG. 15 schematically shows the release of donor quenching during polymerase chain reaction.
Figure 15B:
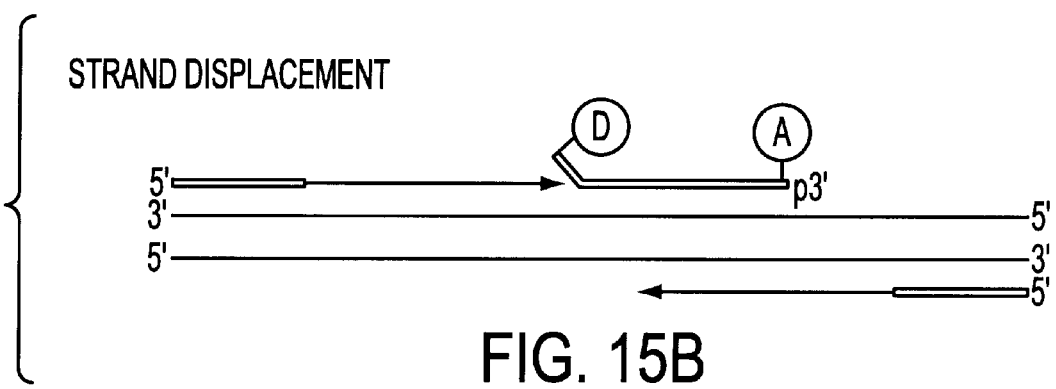
Figure 15C:
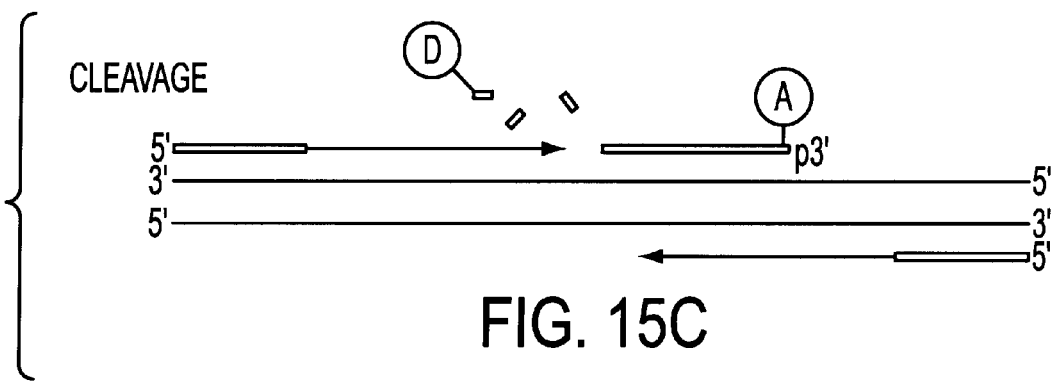
Figure 15D:
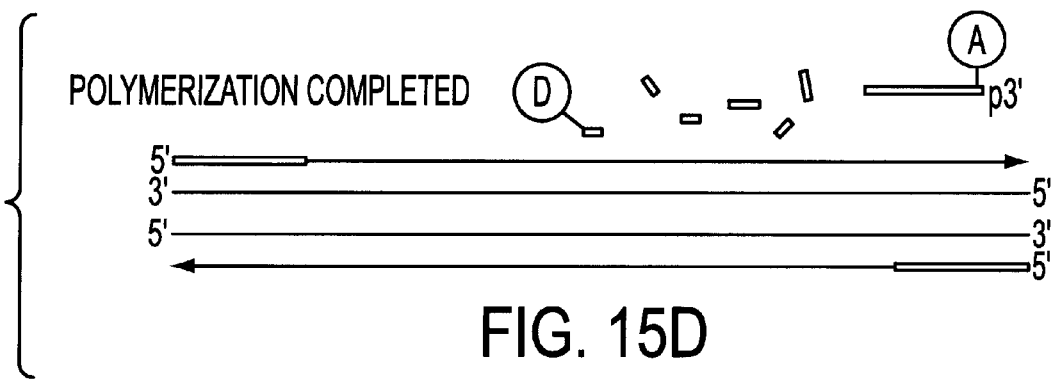
Figure 16A:
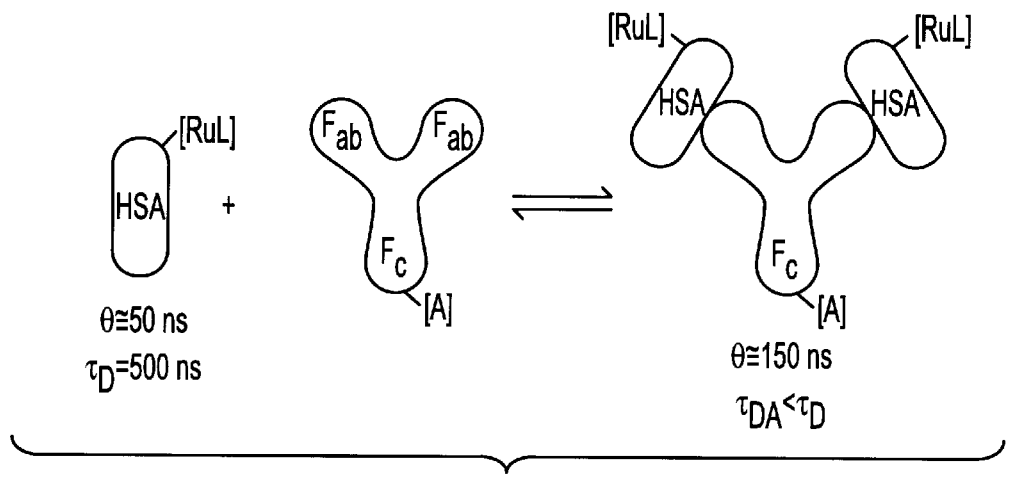
FIG. 16 schematically and graphically shows the energy transfer from a metal- ligand complex donor.
Figure 16B:
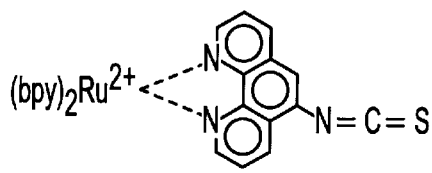
Figure 16C:
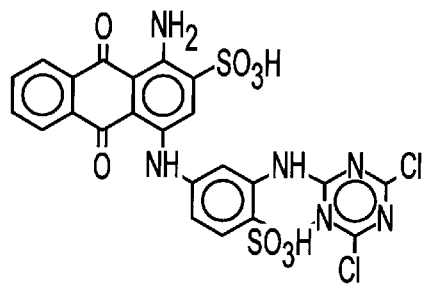
Figure 16D:
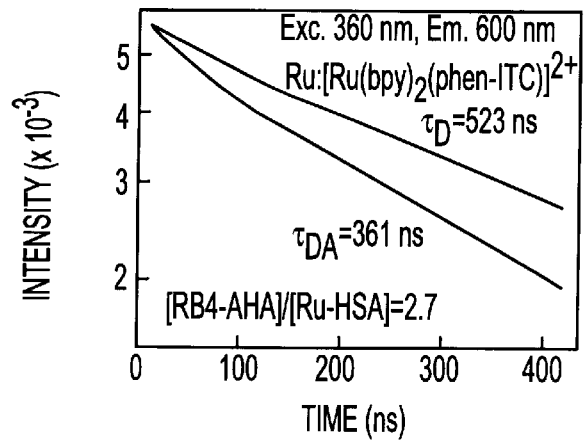
Figure 17:
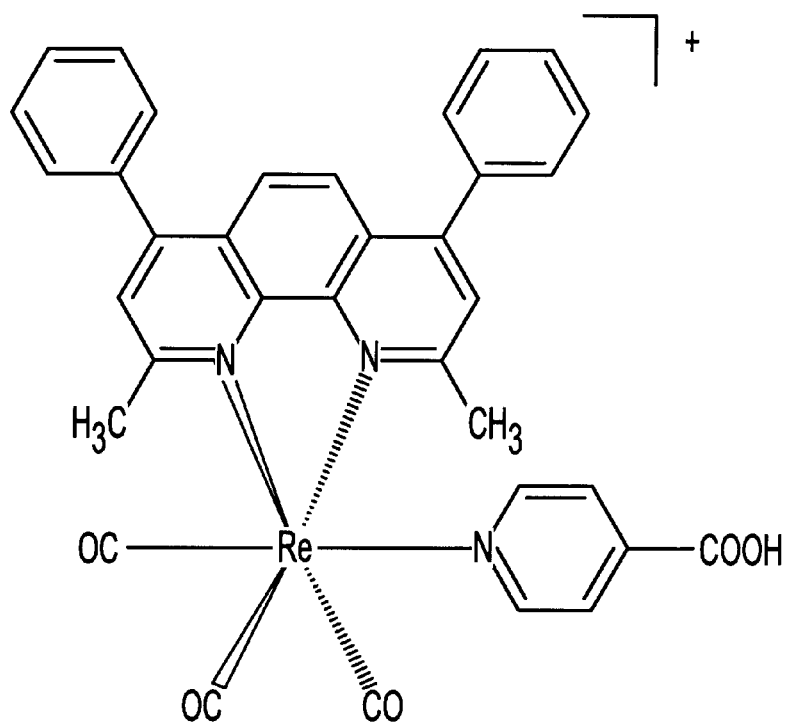
FIG. 17 is the molecular structure for [Re(2,9-dimethyl-4,7-diphenyl-1,10-phenanthroline) $(CO)_3$(isonicotinic acid)]$^+$.
Figure 18:
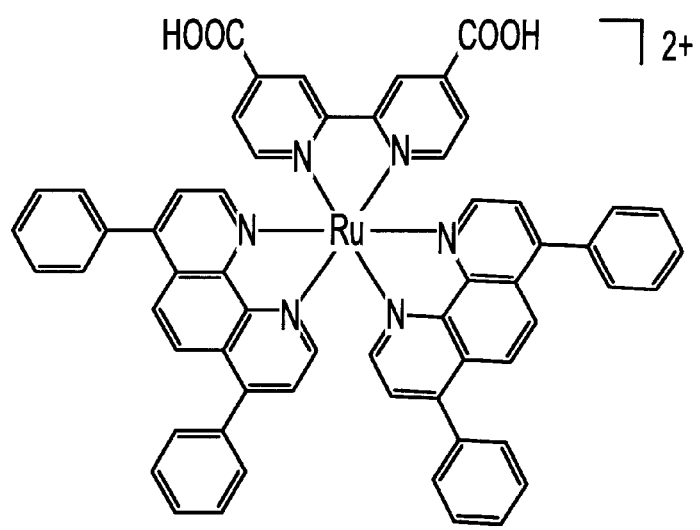
FIG. 18 is the molecular structure for [Ru(4,7-diphenyl-1,10-phenanthroline)$_2$(4,4'-dicarboxylic acid-2,2'-bipyridine)]$^{2+}$.
Figure 19:
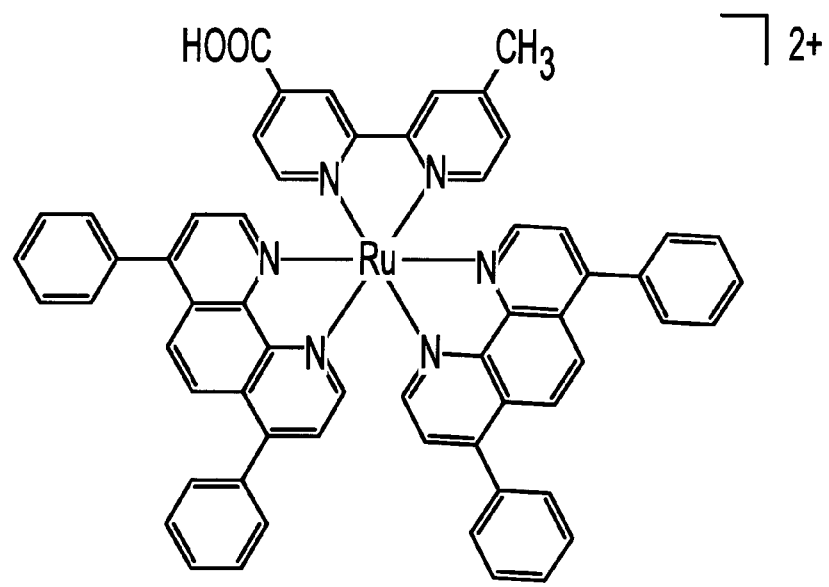
FIG. 19 is the molecular structure for [Ru(4,7-diphenyl-1,10-phenanthroline)$_2$(4-methyl, 4'-carboxylic acid-2,2'-bipyridine)]$^{2+}$.
Figure 20:
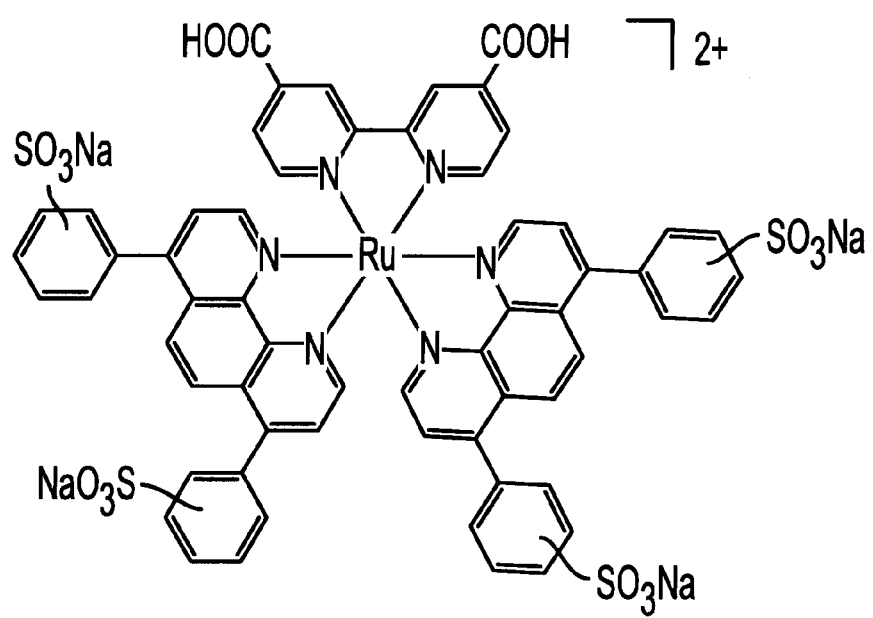
FIG. 20 is the molecular structure for [Ru(4,7-diphenyl-1,10-phenanthroline(SO$_3$Na)$_2$)$_2$(4,4'-dicarboxylic acid-2,2'-bipyridine)]$^{2+}$.
Figure 21:
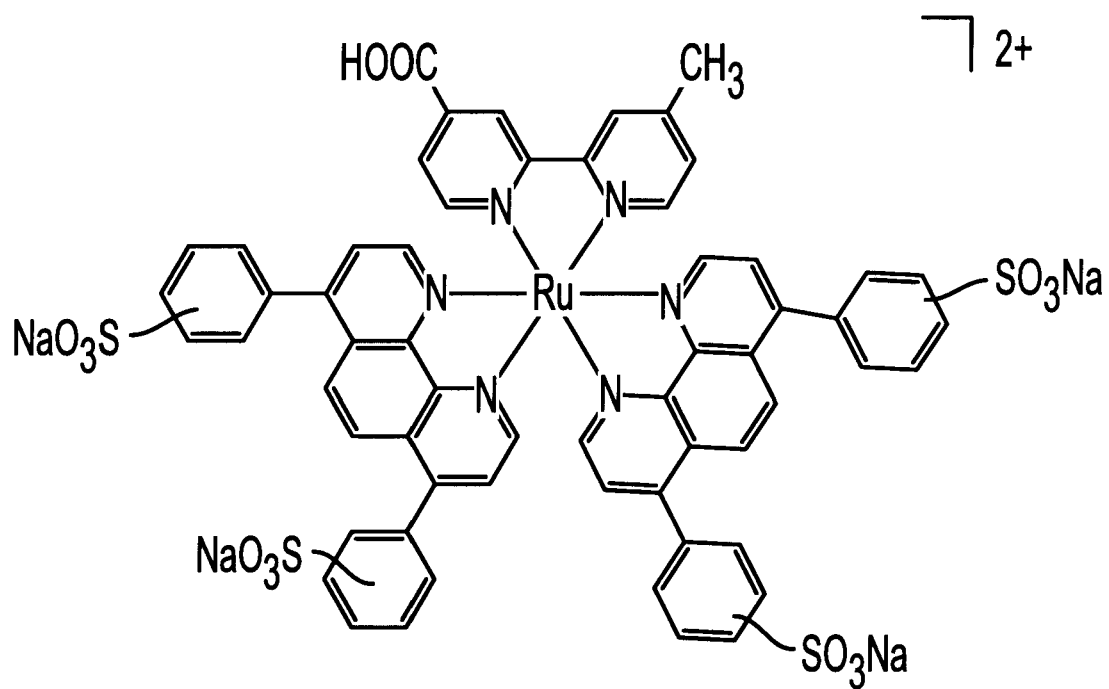
FIG. 21 is the molecular structure for [Ru(4,7-diphenyl-1,10-phenanthroline (SO$_3$Na)$_2$)$_2$(4-methyl, 4'-carboxylic acid-2,2'-bipyridine)]$^{2+}$.
Figure 22:
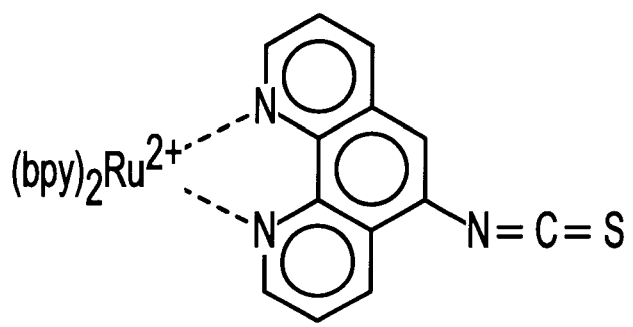
FIG. 22 is the molecular structure for [Ru(2,2'-bipyridyl) (1,10-phenanthroline-9-isothiocyanate)].
Figure 23:
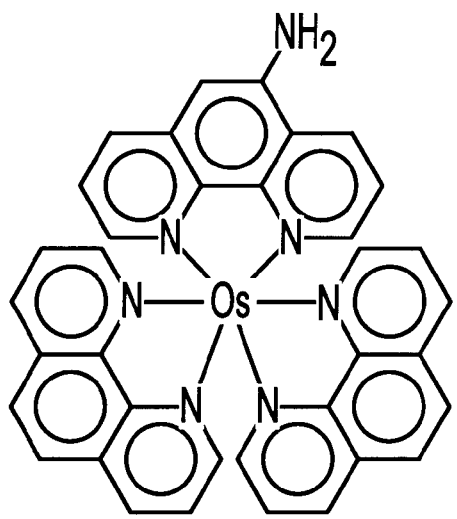
FIG. 23 is the molecular structure for [Os(1,10-phenanthroline)$_2$(5-amino-phenanthroline)]$^{2+}$.
Figure 24:
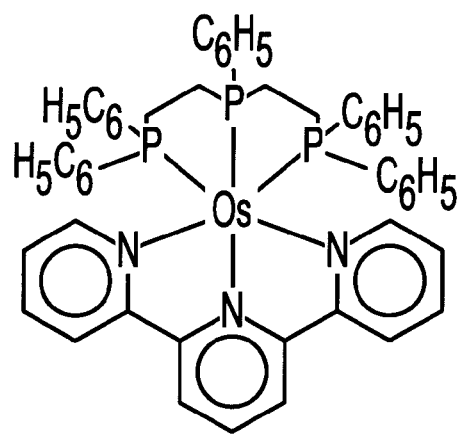
FIG. 24 is the molecular structure for [Os(2,2':6',2"-terpyridine)(Bis(2-diphenylphosphinoethyl)phenyl phosphine)]$^{2+}$.
Figure 25:
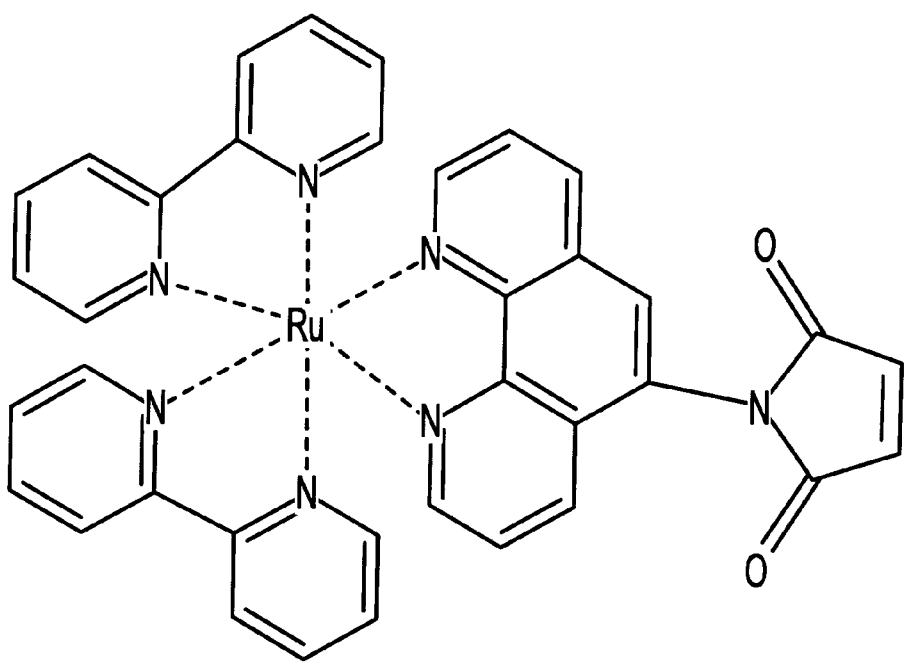
FIG. 25 is the molecular structure for [Ru bis(2,2'-bipyridyl)(phenanthroline-maleamide)].
Figure 26:
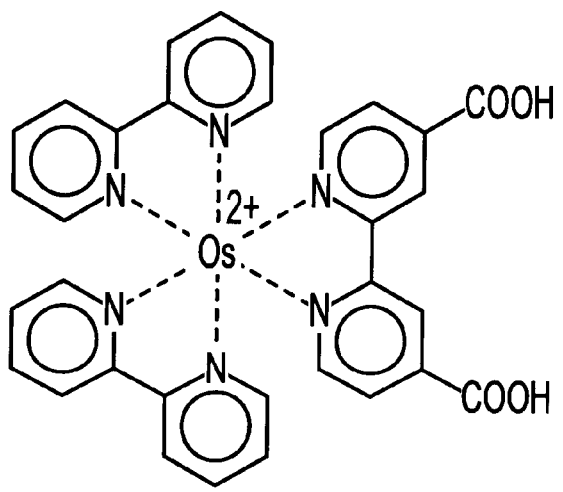
FIG. 26 is the molecular structure for [Os(2,2'-bipyridyl)$_2$ (4,4'-dicarboxylic acid-2,2'-bipyridine)][PF$_6$]$_2$.
Figure 27:
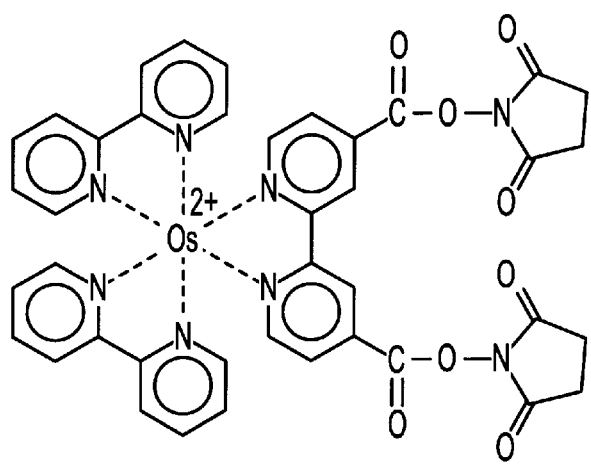
FIG. 27 is the molecular structure for [Os(2,2'-bipyridyl)$_2$ (4,4'-N-hydroxysuccidimide ester-2,2'-bipyridyl)][PF$_6$]$_2$.

In accordance with one embodiment of the present invention, a method is disclosed for detecting the presence of a nucleic acid sequence in a sample, by detecting the fluorescence of metal-ligand complexes.

In accordance with another embodiment of the present invention, a composition is disclosed which includes a fluorescent metal-ligand complex, for detecting the presence of a nucleic acid sequence.

In accordance with another embodiment of the present invention, a diagnostic kit is disclosed which includes a fluorescent metal-ligand complex, for detecting the presence of a nucleic acid sequence.

The invention suggests the use of fluorescent metal-ligand complexes for in situ hybridization. The use of fluorescent metal-ligand complexes, as opposed to the commonly used organic probes such as fluorescein and rhodamine attached to DNA, solves the problem of low sensitivity based on the interfering fluorescence which occurs from all samples.

Fluorescent metal-ligand complexes can provide an increased sensitivity because the long lifetimes will allow off-gating of the prompt autofluorescence.

In addition, all presently used fluorophores are unstable in the presence of continued illumination. Metal-ligand complexes according to the invention solve these problems by displaying long lifetimes, and are thus temporally resolved from the background fluorescence. The large Stoke's shift also allows higher sensitivity by an increased ability to filter out the interfering fluorescence. Furthermore, metal-ligand complexes according to the invention are highly photostable and thus allow sensitivity detection by imaging over a long period of time with continued illumination or with pulse elimination and gated detection.

There are a number of metal-ligand complexes which display luminescence, including complexes containing Co, Cr, Cu, Mo, Ru, Rh, W, Re, Os, Ir, or Pt. In particular, transition metal complexes, especially those with Ru, Os, Re, Rh, Ir, W or Pt, can be used. The metal in the metal-ligand complex is particularly preferably selected from the group consisting of ruthenium, osmium, and rhenium.

A suitable ligand in the metal-ligand complex can be polypyridine, bipyridine, or a related compound, and the ligand can contain a reactive group commonly used for linkage to biological molecules, such as a N-hydroxysuccinimide ester of a carboxylic acid, haloacetyl groups, maleimides, sulfonyl chlorides, and isothiocyanates. Other ligands for such metal-ligand complexes are bipyrazyl, phenanthroline, and related substituted derivatives, or inorganic ligands such as CO, Cl, nitrile and isonitrile. Table 1 shows that the lifetime can be varied by variation of the ligand attached to the metal.

TABLE 1

| L | QY. | τ (ns) | $\lambda_{em\ max}$(nm) |
|---|---|---|---|
| Cl- | 0.005 | 51 | 622 |
| 4-NH$_2$Py | 0.052 | 129 | 597 |
| 4-EtPy | 0.18 | 604 | 567 |
| Py | 0.16 | 669 | 558 |
| P(CH$_3$)$_3$ | 0.27 | 1169 | 544 |
| CH$_3$CN | 0.41 | 1201 | 536 |

Preferred metal-ligand complexes include [Re(2,9-dimethyl-4,7-diphenyl-1,10-phenanthroline) (CO)$_3$ (isonicotinic acid)]$^+$, [Ru(4,7-diphenyl-1,10-phenanthroline)$_2$(4,4'-dicarboxylic acid-2,2'-bipyridine)]$^{2+}$, [Ru(4,7-diphenyl-1,10-phenanthroline)$_2$(4-methyl,4'-carboxylic acid-2,2'-bipyridine)]$^{2+}$, [Ru(4,7-diphenyl-1,10-phenanthroline(SO$_3$Na)$_2$)$_2$(4,4'-dicarboxylic acid-2,2'-bipyridine)]$^{2+}$, [Ru(4,7-diphenyl-1,10-phenanthroline (SO$_3$Na)$_2$)$_2$(4-methyl,4'-carboxylic acid-2,2'-bipyridine)]$^{2+}$, [Ru(2,2'-bipyridyl)(1,10-phenanthroline-9-isothiocyanate)], [Os(1,10-phenanthroline)$_2$(5-amino-phenanthroline)]$^{2+}$, [Os (2,2':6',2"-terpyridine)(Bis(2-diphenylphosphinoethyl) phenyl phosphine)]$^{2+}$, [Ru bis(2,2'-bipyridyl) (phenanthroline-maleamide)], [Os(2,2'-bipyridyl)$_2$(4,4'-dicarboxylic acid-2,2'-bipyridine)][PF$_6$]$_2$, [Os (2,2'-bipyridyl)$_2$(4,4'-N-hydroxysuccidimide ester-2,2'-bipyridyl)][PF$_6$]$_2$, and [Ru(2,2'-bipyridyl)$_2$(4,4'-N-hydroxysuccidimide ester-2,2'-bipyridyl)]$^{2+}$.

Fluorescence in situ hybridization has become widely used in the medical sciences. The DNA to be tested, typically metaphase chromosomes, are exposed to probe DNA. The probe DNA has a base sequence directed toward one or more chromosomes. The probe DNA can be specific for the centromic or telomeric region of chromosomes, or can be directed toward the entire chromosome. DNA probes can also be specific for small regions of DNA representing several genes. The exposure conditions result in denaturation of the chromosomes and hybridization with the probe DNA.

In situ hybridization has been detected using radioactive tracers and autoradiography. For fluorescence in situ hybridization the probe DNA is made as fluorescent as possible by labeling with any fluorophore which does not interfere with hybridization. The reactive amino group attached to the base can be coupled to any of a wide variety of fluorescent probes. One aspect of the fluorescence in situ hybridization technology is that fluorophores can be incorporated with DNA without disruption of the base pairing. DNA can be synthesized with relatively high levels of such nucleotides.

Fluorescence in situ hybridization allows identification of all 23 human chromosomes. It is possible to develop DNA probes which paint each of the human chromosomes. Chromosome painting probes are developed by polymerase chain reaction (PCR) amplification of DNA fragments from chromosomes sorted by flow cytometry. Non-specific binding is presented by adding additional DNA which binds to the most common sequences. However, the potential of fluorescence in situ hybridization for chromosome screening can only be realized if all the chromosomes can be simultaneously visualized. Unfortunately, 23 non-overlapping fluorophores are not presently available.

A variety of methods have been developed for multiple multiplex fluorescence in situ hybridization or spectra karyotyping (SKY). Most methods include the use of multiple DNA probes each containing a different fluorophore. Differences in the chromosomes are revealed by the different colors or ratio of probes bound to each region of the chromosome. The most spectacular advances in fluorescence in situ hybridization have resulted from characterization of the emission spectra, using either an interferometric method or interference filters. By using just five colors for the chromosome paints it is possible to identify each of the 23 chromosomes. These are then assigned easily recognized pseudo colors. These advanced fluorescence in situ hybridization methods can provide a means to detect by gross and simple abnormalities, chromosome rearrangements, monitoring of bone marrow cells following transplantation and cancer chemotherapy.

Fluorescence in situ hybridization has many other important applications besides identifying chromosomes. By use of appropriate DNA sequences fluorescence in situ hybridization can be used to detect the human papillomavirus thought to be responsible for cervical cancer, and determination of fetal sex from amniotic fluid. Many of the applications of fluorescence in situ hybridization rely on computerized imaging and high sensitivity CCD detection. Fluorescence in situ hybridization technology represents a combination of modern optics, molecular biology and fluorescence spectroscopy.

The metal-ligand complexes of the present invention may be used in place of the known fluorophores in any suitable in situ hybridization method.

In situ hybridization has numerous applications. Examples of uses for in situ hybridization include, but are not limited to, detection of human papillomavirus, detection of the messenger RNA for ovulation hormone, painting of chromosomes for identification of the chromosomes, detection of chromosome rearrangements, delineation of break points and chromosome abnormalities, cancer detection, detection of the gene for muscular dystrophy, and detection of sperm in cases of alleged sexual assault.

One embodiment of the present invention utilizes a metal-ligand complex which is capable of emitting polarized fluorescent light after being excited with linearly polarized electromagnetic light energy. A detailed description of this method is disclosed in U.S. application Ser. No. 08/330,743, incorporated herein by reference.

Another embodiment of the present invention utilizes fluorescent donor/acceptor pairs, or intercalating dyes, to detect DNA hybridization.

In another embodiment of the present invention, the release of the metal-ligand complex is quenched by an acceptor prior to cleavage of the probe. Such dequenching assays are used in PCR. A description of the prior PCR method is disclosed in Gibson, U. E. M., Heid, C. A., and Williams, P. M., "A Novel Method for Real Time Quantitative RT-PCR," *Genome Research* 6:995–1001 (1996).

A further embodiment of the present invention utilizes selection of complexes with different lifetimes, so that the presence of the nucleic acid can be identified by the decay time of the label. Lifetime measurements are presently possible by measurements using either the time domain or the frequency domain, but the instrumentation is complex for nanosecond decay times. Alternately, fluorescence lifetime imaging of the gels which contain the labeled DNA can be utilized.

A description of a lifetime imaging apparatus is provided in U.S. Pat. No. 5,485,530, incorporated herein by reference.

Descriptions of the prior fluorescence lifetime methods are disclosed in the following references:

H. Szmacinski, J. R. Lakowicz, M. L. Johnson, "Fluorescence Lifetime Imaging Microscopy: Homodyne Technique Using High-Speed Gated Image Intensifier," *Methods in Enzymology*, 240:723–748 (1994).

J. R. Lakowicz, H. Szmacinski, K. Nowaczyk, W. J. Lederer, M. S. Kirby, and M. L. Johnson, "Fluorescence lifetime imaging of intracellular calcium in COS cells using Quin-2," *Cell Calcium* 15:7–27 (1994).

J. R. Lakowicz, P. A. Koen, H. Szmacinski, I. Gryczynski, and J. Kusba, "Emerging Biomedical and Advanced Applications of Time-Resolved Fluorescence Spectroscopy," *Journal of Fluorescence* 4:117–136 (1994).

J. R. Lakowicz, H. Szmacinski, K. Nowaczyk, K. W. Berndt, and M. Johnson, "Fluorescence Lifetime Imaging," *Analytical Biochemistry* 202:316–330 (1992).

J. R. Lakowicz, H. Szmacinski, K. Nowaczyk, and M. L. Johnson, "Fluorescence lifetime imaging of free and protein-bound NADH," *Proc. Natl. Acad. Sci., U.S.A.* 89:1271–1275 (1992).

In another embodiment of the invention, capillary electrophoresis is used to determine the base sequence. Descriptions of prior capillary electrophoresis methods are disclosed in the following references:

J. A. Brumbaugh, L. R. Middendorf, D. L. Grone, and J. L. Ruth, "Continuous on-line DNA sequencing using oligodeoxynucleotide primers with multiple fluorophores," *Proc. Natl. Acad. Sci. U.S.A.* 85:5610–14 (1988).

H. Swerdlow, J. Z. Zhang, D. Y. Chen, H. R. Harke, R. Grey, S. Wu, and N. J. Dovichi, "Three DNA Sequencing Methods Using Capillary Gel Electrophoresis and Laser-Induced Fluorescence," *Anal. Chem.* 63:2835–2841 (1991).

X. C. Huang, M. A. Quesada, and R. A. Mathies, "DNA Sequencing Using Capillary Array Electrophoresis," *Anal. Chem.*, 64:2149–2154 (1992).

S. Carson, A. S. Cohen, A. Belenkii, M. C. Ruiz-Martinez, J. Berka, and B. L. Karger, "DNA Sequencing by Capillary Electrophoresis: Use of a Two-Laser-Two-Window Intensified Diode Array Detection System," *Anal. Chem.* 65:3219–3226 (1993).

K. Ueno and E. S. Yeung, "Simultaneous Monitoring of DNA Fragments Separated By Electrophoresis in a Multiplexed Array of 100 Capillaries," *Anal. Chem.*, 66: 1424–1431 (1994).

L. R. Middendorf, J. A. Brumbaugh, D. L. Grone, C. A. Morgan, and J. L. Ruth, "Large scale DNA sequencing," *American Biotechnology Laboratory*, August 1988.

DNA chip technology, which utilizes light directed matrices, may be used in another embodiment of the present invention. This technology is available in Affymetrix's GeneChip™ and Hyseq's SuperChips™.

Descriptions of prior DNA chip technology are disclosed in the following references:

S. P. A. Fodor, "Massively Parallel Genomics," *Science* 277:393–395(1997).

A. Caviani Pease, D. Solas, E. J. Sullivan, M. T. Cronin, C. P. Holmes, and S. P. A. Fodor, "Light-generated oligonulceotide arrays for rapid DNA sequence analysis," *Proc. Natl. Acad. Sci. U.S.A.* 91:5022–5026 (1994).

R. J. Lipshutz, D. Morris, M. Chee, E. Hubbell, M. J. Kozal, N. Shah, N. Shen, R. Yang, and S. P. A. Fodor, "Using Oligonucleotide Probe Arrays To Access Genetic Diversity," *Biotechniques* 19:442–448 (1995).

M. T. Cronin, R. V. Fucini, S. M. Kim, R. S. Masino, R. M. Wespi, and C. G. Miyada, "Cystic Fibrosis Mutation Detection by Hybridization to Light-Generated DNA Probe Arrays," *Human Mutation* 7:244–255 (1996).

Figure 28:
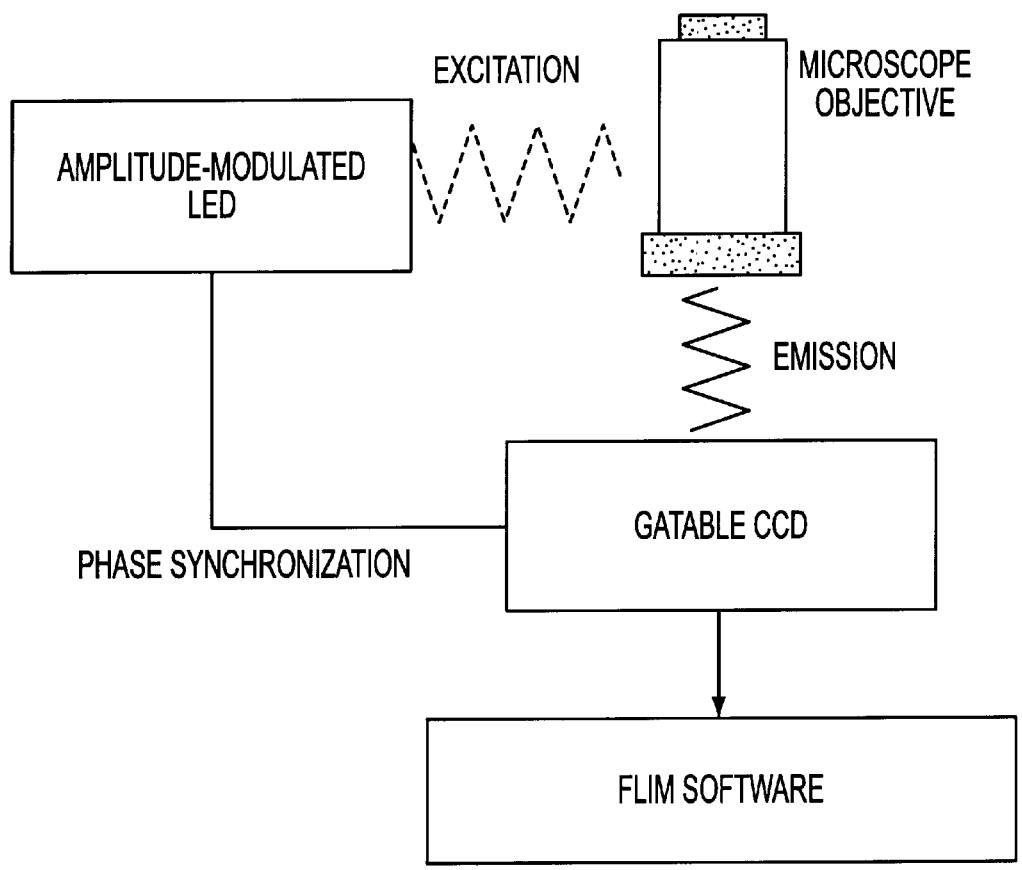
FIG. 28 is a schematic of a solid state lifetime imager. The excitation can be an amplitude-modulated LED and the emission detected with a gatable CCD.

The capillary tubes or the DNA chips are imaged using CCD technology and the gain modulated image intensifier. This techniques allows the decay times to be measured at each point in the image, without single spot pixel by pixel scanning. A self-gated CCD camera, which does not have an image intensifier, can be used with long-lived metal ligand complexes. The use of a self-gated CCD camera is simpler than using an image intensifier. Long-lifetime metal ligand complexes are ideal for use with CCD cameras, which have relatively slow speeds (FIG. 28).

The invention is further illustrated by the following examples, which are not intended to be limiting.

EXAMPLE 1

A fluorescent metal-ligand complex having the formula [Ru(2,2'-bipyridyl)$_2$(4,4'-N-hydroxysuccidimide ester-2,2'-bipyridyl)$^{2+}$ (FIG. 9) is coupled to an oligonucleotide containing a reactive amine to form a probe. The amount of metal-ligand complex is about ten-fold excess over the amount of oligonucleotide, and the reaction is carried out under basic conditions near pH 8, using a carbonate buffer which is not nucleophilic and does not react with the metal-ligand complex probe. Following purification by any suitable known procedures, the metal-ligand complex probe is added to a sample believed to contain a nucleic acid sequence complimentary to the oligonucleotide sequence of the probe, and the reaction product is formed. The mixture is exposed to radiation near 450 nm, and a long pass optical filter is utilized to detect the emission near 600 nm. Detection can be performed as a steady state measurement, or with time-gated detection with off-gating of the autofluorescence and on-gating of the long-lived metal-ligand complex fluorescence. Binding may also be detected by fluorescence polarization, in which case the excitation of the emission beams will contain polarizers.

Since many modifications, variations, and changes in detail may be made to the described embodiments, it is intended that all matter in the foregoing description and shown in the accompanying drawings be interpreted as illustrative and not in a limiting sense.

What is claimed is:

1. A method for detecting the presence of a nucleic acid sequence in a sample comprising the steps of:
   a) adding a probe labeled with a fluorescent metal-ligand complex to a sample that contains said nucleic acid sequence to form a mixture containing a reaction product;
   b) exposing said mixture to an exciting amount of radiation;
   c) detecting fluorescence of said metal-ligand complex; and
   d) determining presence of said nucleic acid sequence based on fluorescence of said metal-ligand complex,
wherein said fluorescent metal ligand complex is selected from the group consisting of [Re(2,9-dimethyl-4,7-diphenyl-1,10-phenanthroline) $(CO)_3$(isonicotinic acid)]$^+$, [Ru(4,7-diphenyl-1,10-phenanthroline)$_2$(4,4'-dicarboxylic acid-2,2'-bipyridine)]$^{2+}$, [Ru(4,7-diphenyl-1,10-phenanthroline)$_2$(4-methyl,4'-carboxylic acid-2,2'-bipyridine)]$^{2+}$, (Ru(4,7-diphenyl-1,10-phenanthroline $(SO_3Na)_2)_2$(4,4'-dicarboxylic acid-2,2'-bipyridine)]$^{2+}$, [Ru (4,7-diphenyl-1,10-phenanthroline$(SO_3Na)_2)_2$(4-methyl,4'-carboxylic acid-2,2'-bipyridine)]$^{2+}$, [Ru(2,2'-bipyridyl)(1,10-phenanthroline-9-isothiocyanate)], [Os (1,10-phenanthroline)$_2$(5-amino-phenanthroline)]$^{2+}$, [Os(2,2':6',2''-terpyridine)(Bis(2-diphenylphosphinoethyl)phenyl phosphine)]$^{2+}$, [Ru bis(2,2'-bipyridyl)(phenanthroline-maleamide)], [Os(2,2'-bipyridyl)$_2$(4,4'-dicarboxylic acid-2,2'-bipyridine)][PF$_6$]$_2$, [Os(2,2'-bipyridyl)$_2$(4,4'-N-hydroxysuccidimide ester 2,2'-bipyridyl)][PF$_6$]$_2$, and [Ru(2,2'-bipyridyl)$_2$(4,4'-N-hydroxysuccidimide ester-2,2'-bipyridyl)]$^{2+}$.

2. A method for detecting the presence of a nucleic acid sequence in a sample comprising the steps of:
   a) adding a probe labeled with a fluorescent metal-ligand complex to a sample that contains said nucleic acid sequence to form a mixture containing a reaction product;
   b) exposing said mixture to an exciting amount of radiation;
   c) detecting fluorescence of said metal-ligand complex; and
   d) determining presence of said nucleic acid sequence based on fluorescence of said metal-ligand complex,
wherein said metal-ligand complex is capable of emitting polarized fluorescent light after being excited with linearly polarized electromagnetic light energy;
   wherein said radiation is linearly polarized electromagnetic light energy which causes said mixture to emit polarized fluorescent light;
   wherein said detection is measurement of polarization of fluorescent light emission;
   wherein prior to forming said reaction product, said oligonucleotide is exposed to said linearly polarized electromagnetic light energy and polarization of fluorescent light is measured; and
   wherein said determination of presence of said nucleic acid utilizes the change in polarization of fluorescent light emission of the oligonucleotide and polarization of fluorescent light emission of the mixture.

3. A composition for detecting the presence of a nucleic acid sequence, comprising a fluorescent metal-ligand complex coupled to an oligonucleotide having a sequence complementary to said nucleic acid sequence, wherein said fluorescent metal ligand complex is selected from the group consisting of [Re(2,9-dimethyl-4,7-diphenyl-1,10-phenanthroline) $(CO)_3$(isonicotinic acid)]$^+$, [Ru(4,7-diphenyl-1,10-phenanthroline)$_2$(4,4'-dicarboxylic acid-2,2'-bipyridine)]$^{2+}$, [Ru(4,7-diphenyl-1,10-phenanthroline)$_2$(4-methyl,4'-carboxylic acid-2,2'-bipyridine)]$^{2+}$, [Ru(4,7-diphenyl-1,10-phenanthroline $(SO_3Na)_2)_2$(4,4'-dicarboxylic acid-2,2'-bipyridine)]$^{2+}$, [Ru(4,7-diphenyl-1,10-phenanthroline $(SO_3Na)_2)_2$(4-methyl,4'-carboxylic acid-2,2'-bipyridine)]$^{2+}$, [Ru(2,2'-bipyridyl)(1,10-phenanthroline-9-isothiocyanate)], [Os(1,10-phenanthroline)$_2$(5-amino-phenanthroline)]$^{2+}$, [Os(2,2':6',2''-terpyridine)(Bis(2-diphenylphosphinoethyl)phenyl phosphine)]$^{2-}$, [Ru bis(2,2'-bipyridyl)(phenanthroline-maleamide)], [Os(2,2'-bipyridyl)$_2$ (4,4'-dicarboxylic acid-2,2'-bipyridine)][PF$_6$]$_2$, [Os(2,2'-bipyridyl)$_2$(4,4'-N-hydroxysuccidimide ester-2,2'-bipyridyl)][PF$_6$]$_2$, and [Ru(2,2'-bipyridyl)$_2$(4,4'-N-hydroxysuccidimide ester-2,2'-bipyridyl)]$^{2+}$.

\* \* \* \* \*